US012198788B2

(12) United States Patent
Stahl

(10) Patent No.: US 12,198,788 B2
(45) Date of Patent: Jan. 14, 2025

(54) SYSTEM FOR DETECTING AN INTRAORAL DISEASE AND DETERMINING A PERSONALIZED TREATMENT SCHEME AND METHOD OF DOING SAME

(71) Applicant: CANNIBITE BVBA, Mortsel (BE)

(72) Inventor: Veronica Stahl, Mortsel (BE)

(73) Assignee: Cannibite BVBA (BE)

( * ) Notice: Subject to any disclaimer, the term of this patent is extended or adjusted under 35 U.S.C. 154(b) by 681 days.

(21) Appl. No.: 16/753,386

(22) PCT Filed: Oct. 4, 2018

(86) PCT No.: PCT/IL2018/051084
§ 371 (c)(1),
(2) Date: Apr. 3, 2020

(87) PCT Pub. No.: WO2019/069312
PCT Pub. Date: Apr. 11, 2019

(65) Prior Publication Data
US 2020/0286597 A1 Sep. 10, 2020

Related U.S. Application Data

(60) Provisional application No. 62/657,953, filed on Apr. 16, 2018, provisional application No. 62/567,763, filed on Oct. 4, 2017.

(51) Int. Cl.
*G16H 10/40* (2018.01)
*A61B 10/00* (2006.01)
(Continued)

(52) U.S. Cl.
CPC ......... *G16H 10/40* (2018.01); *A61B 10/0051* (2013.01); *A61K 8/368* (2013.01);
(Continued)

(58) Field of Classification Search
None
See application file for complete search history.

(56) References Cited

U.S. PATENT DOCUMENTS 8,920,340 B2    12/2014  Gittins et al.
2003/0157637 A1  8/2003  Reynolds et al.
(Continued)

FOREIGN PATENT DOCUMENTS

WO    WO-2018011813 A1 *  1/2018  ........... A61K 31/065

OTHER PUBLICATIONS

PCT International Search Report and Written Opinion for PCT Patent Application No. PCT/IL2018/051084 mailed on Apr. 15, 2019, 13 pages.
(Continued)

*Primary Examiner* — Celeste A Roney
(74) *Attorney, Agent, or Firm* — McAndrews, Held & Malloy, Ltd.

(57) ABSTRACT

The current invention discloses a system for detecting an intraoral disease and determining a personalized treatment scheme; the system comprising: a. a reservoir configured for accommodating a sample of a biologic material collected in an oral cavity of a patient; b. a first detector for detecting a first substance originating from bacteria; c. a second detector for detecting a second substance originating from at least one of an immune and an inflammatory system of the patient; d. a control unit configured for operatively receiving signals from the first and second detectors and analyzing the signals; and e. display and communication means configured for presenting results of signal analysis; wherein the control unit is configured for determining said treatment scheme comprising relevant antimicrobial compositions and a dosing frequency thereof. Additionally, the present invention recommends customized cannabis-based oral care products.

21 Claims, 10 Drawing Sheets

(51) Int. Cl.
  *A61K 8/368*   (2006.01)
  *A61K 8/49*    (2006.01)
  *A61K 8/9789*  (2017.01)
  *G16H 10/60*   (2018.01)
  *G16H 20/10*   (2018.01)

(52) U.S. Cl.
  CPC ............ *A61K 8/498* (2013.01); *A61K 8/9789* (2017.08); *G16H 10/60* (2018.01); *G16H 20/10* (2018.01); *A61K 2800/92* (2013.01)

(56) References Cited

U.S. PATENT DOCUMENTS

| | | | |
|---|---|---|---|
| 2007/0037225 | A1 | 2/2007 | Metzger et al. |
| 2007/0270377 | A1* | 11/2007 | Kawakami ............. A61Q 11/00 435/253.4 |
| 2009/0305296 | A1* | 12/2009 | Bengtsson ......... G01N 33/6869 435/7.1 |
| 2010/0331641 | A1 | 12/2010 | Bangera et al. |
| 2011/0251096 | A1 | 10/2011 | Southern |
| 2016/0166498 | A1* | 6/2016 | Anastassov ............ A61Q 11/00 424/58 |
| 2019/0365667 | A1* | 12/2019 | Wright .................... A61K 47/22 |
| 2020/0286597 | A1 | 9/2020 | Stahl |

OTHER PUBLICATIONS

Veronica Stahl et al., Comparison of Efficacy of Cannabinoids Versus Commercial Oral Care Products in Reducing Bacterial Content from Dental Plaque: A Preliminary Observation, Cureus, vol. 12(1), Jan. 29, 2020, 9 pages.

* cited by examiner

SYSTEM FOR DETECTING AN INTRAORAL DISEASE AND DETERMINING A PERSONALIZED TREATMENT SCHEME AND METHOD OF DOING SAME

CROSS-REFERENCE TO RELATED APPLICATIONS

The present application is a National Phase Entry of PCT International Application No. PCT/IL2018/051084 which was filed on Oct. 4, 2018, which claims priority to provisional patent application Ser. No. 62/567,763, filed Oct. 4, 2017 and provisional patent application Ser. No. 62/657,953, filed Apr. 16, 2018, all of which are hereby incorporated by reference in their entireties.

FIELD OF THE INVENTION

The present invention generally pertains to a system for detecting periodontal disease. The present invention further relates to a method and system for the diagnosis and prediction of risk for progress of periodontal disease and provides means and methods for personalized detection and recommendation of customized treatment. Additionally, the present invention recommends customized cannabis-based oral care products.

BACKGROUND OF THE INVENTION

Oral hygiene is the practice of keeping one's mouth clean and free of disease (dental caries) and other problems (e.g. bad breath, halitosis) by regular brushing and cleaning between the teeth. It is important that oral hygiene be carried out on a regular basis to enable prevention of dental disease. The most common types of dental disease are tooth decay (cavities, dental caries) and gum diseases, including gingivitis, and periodontitis as well as bad breath. Bacteria play a major role in many oral health issues. For example, tooth decay and periodontal disease are often caused by undesirable bacteria in the mouth. Bacteria also interact with proteins present in saliva to form a film, known as plaque that coats the teeth. If this plaque is not removed, acids produced by the bacteria can attack the teeth resulting in tooth decay. The plaque also may attack the soft gum tissue of the mouth leading to tooth loss in adults.

Many products such as mouthwashes, toothpastes and interdental cleaners are available, yet there remains a long felt and unmet need for improved oral and dental products to be personalized to be effective against harmful bacteria in the individual patient oral microbiome, oral and dental flora.

U.S. Pat. No. 8,920,340 discloses a toothbrush for identifying the existence of an oral condition in a subject. The toothbrush includes: a body configured for collecting a sample from an oral cavity. The body encloses a reservoir for storing the sample, a detector capable of detecting the existence of a marker within said sample and an indicator capable of being actuated by a signal from the detector.

US 20090305296 discloses a test kit is disclosed for diagnosing periodontal disease in a patient by analyzing a sample from the oral cavity of the patient. The test kit includes at least a first detection assay for detection of a first substance originating from bacteria and at least a second detection assay for detection of a second substance originating from the immune or inflammatory system of the patient.

The technical solutions known in the art provide analytical means for diagnosing periodontal disease. The aforesaid technical solutions, however, are unable of determining an optimal treatment of the disease depending on the patient's condition. Thus, there is a long-felt and unmet need for providing a device capable of detecting the patient's condition and informing a medical professional or the patient about the optimal treatment of the detected patient's condition.

SUMMARY OF THE INVENTION

It is thus one object of the present invention to disclose a system for detecting an intraoral disease and determining a personalized treatment scheme; said system comprising:
 a. a reservoir configured for accommodating a sample of a biologic material collected in an oral cavity of a patient;
 b. a first detector for detecting a first substance originating from bacteria;
 c. a second detector for detecting a second substance originating from at least one of an immune and an inflammatory system of the patient;
 d. a control unit configured for operatively receiving signals from said first and second detectors and analyzing said signals; and
 e. display and communication means configured for presenting results of signal analysis;
wherein said control unit is configured for determining said treatment scheme comprising relevant antimicrobial compositions and a dosing frequency thereof.

It is another object of the invention to disclose a system as defined above, said system comprising means for collecting said sample of a biologic material from said patient's oral cavity.

It is another object of the invention to disclose a system as defined above, wherein said reservoir, said first detector and said second detector are arranged into an integral part connectable to computer means selected from the group consisting of a desktop computer, a laptop computer, a tablet, a smartphone and any combination thereof having a nontransitive computer-readable medium comprising commands for analyzing said signals and determining said treatment scheme.

It is another object of the invention to disclose a system as defined above, wherein said first substance is a bacterial virulence product.

It is another object of the invention to disclose a system as defined above, wherein said first substance is an enzyme.

It is another object of the invention to disclose a system as defined above, wherein said enzyme is a protease.

It is another object of the invention to disclose a system as defined above, wherein said protease is selected from the group consisting of arg-gingipain from *Porphyromonas gingivalis* and a 48 kDa protease from *Bacteroides forsythus*.

It is another object of the invention to disclose a system as defined above, wherein said first substance is a toxin.

It is another object of the invention to disclose a system as defined above, wherein said toxin is a leukotoxin from *Actinobacillus actinomycetemcomitans*.

It is another object of the invention to disclose a system as defined above, wherein said second substance is a leukocyte product.

It is another object of the invention to disclose a system as defined above, wherein said leukocyte product is a natural serine protease.

It is another object of the invention to disclose a system as defined above, wherein said natural serine protease is a human neutrophil elastase.

It is another object of the invention to disclose a system as defined above, wherein said second substance is a cytokine.

It is another object of the invention to disclose a system as defined above, wherein said cytokine is an interleukin.

It is another object of the invention to disclose a system as defined above, wherein said interleukin is chosen from among interleukin-1β, interleukin-6 and interleukin-8.

It is another object of the invention to disclose a system as defined above, wherein said cytokine is an inflammatory mediator.

It is another object of the invention to disclose a system as defined above, wherein said inflammatory mediator is selected from the group consisting of tumour necrosis factor-α and prostaglandin $E_2$.

It is thus one object of the present invention to disclose a system for detecting an intraoral disease and determining a treatment scheme; said system comprising:
- a. a server configured for processing and storing patients' medical data;
- b. a plurality of devices for detecting an intraoral disease; each device comprising:
  - i. a reservoir configured for accommodating a sample of a biologic material collected in an oral cavity of a patient;
  - ii. a first detector for detecting a first substance originating from bacteria;
  - iii. a second detector for detecting a second substance originating from at least one of an immune and an inflammatory system of the patient; and
  - iv. a control unit configured for operatively receiving signals from said first and second detectors and analyzing said signals;
  - v. display means configured for presenting results of signal analysis;
  wherein said server is configured for determining an antimicrobial composition treatment scheme comprising a type of relevant cannabinoid and a dosing frequency thereof and communicating said It is thus one object of the present invention to disclose a method of detecting an intraoral disease and determining a treatment scheme; said method comprising steps:
- a. providing a system for detecting an intraoral disease and determining a treatment scheme; said system comprising:
  - i. a reservoir configured for accommodating a sample of a biologic material collected in an oral cavity of a patient;
  - ii. a first detector for detecting a first substance originating from bacteria;
  - iii. a second detector for detecting a second substance originating from at least one of an immune and an inflammatory system of the patient; and
  - iv. a control unit configured for operatively receiving signals from said first and second detectors and analyzing said signals;
  - v. wherein said control unit is configured for determining said treatment scheme comprising a type of relevant cannabinoid and a dosing frequency thereof;
- b. collecting a sample of biologic material from said oral cavity of said patient;
- c. placing said sample of biologic material into said reservoir;
- d. detecting said first substance within said sample of biologic material;
- e. detecting said second substance within said sample of biologic material;
- f. receiving signals from said first and second detectors;
- g. analyzing said first and second signals in a correlational manner;
- h. determining said treatment scheme comprising a type of relevant cannabinoid and a dosing frequency thereof.

It is another object of the invention to disclose a method as defined above, wherein said first substance is a bacterial virulence product.

It is another object of the invention to disclose a method as defined above, wherein said first substance is an enzyme.

It is another object of the invention to disclose a method as defined above, wherein said enzyme is a protease.

It is another object of the invention to disclose a method as defined above, wherein said protease is selected from the group consisting of arg-gingipain from *Porphyromonas gingivalis* and a 48 kDa protease from *Bacteroides forsythus*.

It is another object of the invention to disclose a method as defined above, wherein said first substance is a toxin.

It is another object of the invention to disclose a method as defined above, wherein said toxin is a leukotoxin from *Actinobacillus actinomycetemcomitans*.

It is another object of the invention to disclose a method as defined above, wherein said second substance is a leukocyte product.

It is another object of the invention to disclose a method as defined above, wherein said leukocyte product is a natural serine protease.

It is another object of the invention to disclose a method as defined above, wherein said natural serine protease is a human neutrophil elastase.

It is another object of the invention to disclose a method as defined above, wherein said second substance is a cytokine.

It is another object of the invention to disclose a method as defined above, wherein said cytokine is an interleukin.

It is another object of the invention to disclose a method as defined above, wherein said interleukin is chosen from among interleukin-1β, interleukin-6 and interleukin-8.

It is another object of the invention to disclose a method as defined above, wherein said cytokine is an inflammatory mediator.

It is another object of the invention to disclose a method as defined above, wherein said inflammatory mediator is selected from the group consisting of tumour necrosis factor-α and prostaglandin $E_2$.

It is thus one object of the present invention to disclose a system for providing a personalized oral care formulation for a patient; said system comprising:
- a. a detection module for detecting characteristics of a bacterial oral infection;
- b. an in vitro test module for testing antibacterial activity of a panel of antimicrobial compounds;
- c. an oral care compounding module for receiving data from said in vitro test module concerning effectiveness of members of said panel on said antibacterial activity;
- d. an oral care compound cartridge containing said oral care formulation;
wherein said oral care compounding module provides instructions on producing said oral care formulation containing an optimized selection of members of said panel of antimicrobial compounds or compositions and said oral care compound cartridge is configured to be operationally connected to an end user toothpaste package, dentifrice package or mouthwash container.

It is another object of the invention to disclose a system as defined above, wherein said oral care formulation is selected from the group comprising of an oral formulation is in the form of a mouthwash, dentifrice or toothpaste.

It is another object of the invention to disclose a system as defined above, wherein said panel of antimicrobial compounds or compositions comprises cannabinoids, chlorhexidine compounds, chlorhexidine gluconate, cationic antimicrobial compounds, essential oils, fluoride compounds, chlamoxicillin, amoxicillin/clavulanate, clindamycin, metronidazole or any combination thereof.

It is another object of the invention to disclose a system as defined above, wherein said oral care compounding module is operationally connected to an oral care formulation production line.

It is another object of the invention to disclose a system as defined above, wherein said system additionally comprises a database for storing output of patient results from detection module, in vitro test module or oral care compounding module or any combination thereof.

It is another object of the invention to disclose a system as defined above, wherein said system additionally comprises a server configured for processing and storing patients' medical and/or dental data.

It is another object of the invention to disclose a system as defined above, wherein said composition of an oral formulation is in the form of a mouthwash, dentifrice or toothpaste.

It is another object of the invention to disclose a system as defined above, wherein said panel comprises cannabinoids THCA, CBDA, cannabinolic acid (CBNA), cannabigerolic acid (CBGA), cannabichromenic acid (CBCA) and cannabinodiolic acid (CBNDA) or any combination thereof.

It is another object of the invention to disclose a system as defined above, wherein said panel comprises cannabis related substances selected from the group consisting of Dronabinol (2), Nabiximols, Nabilone, THC, CBD, Cannabidiol, Levonantradol Ajulemic acid, (CT3), ECP002A, Natural Δ9-THC, Cannabichromenes, Cannabichromene (CBC), Cannabichromenic acid (CBCA), Cannabichromevarin (CBCV), Cannabichromevarinic acid (CBCVA), Cannabidiol Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoins, Cannabielsoic acid B (CBEA-B), Cannabielsoin (CBE), Cannabielsoin acid A (CBEA-A), Cannabigerols, Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA, Cannabinols and cannabinodiols, Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriols, 10-Ethoxy-9-hydroxy-delta-6a-tetrahydrocannabinol, 8,9-Dihydroxy-delta-6a-tetrahydrocannabinol, Cannabitriol (CBT), Cannabitriolvarin (CBTV), Delta-8-tetrahydrocannabinols, Delta-8-tetrahydrocannabinol ($\Delta^8$-THC), Delta-8-tetrahydrocannabinolic acid ($\Delta^8$-THCA), Delta-9-tetrahydrocannabinols, Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA) 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC), 3,4,5,6-Tetrahydro-7-hydroxy-alpha-alpha-2-trimethyl-9-n-propyl-2,6-methano-2H-1-benzoxocin-5-methanol, or OH-iso-HHCV or any combination thereof.

It is another object of the invention to disclose a system as defined above, wherein said panel comprises compositions selected from a group consisting of chlorhexidine compounds, chlorhexidine gluconate, cationic antimicrobial compounds, essential oils, fluoride compounds, chlamoxicillin, amoxicillin/clavulanate, clindamycin, metronidazole, punica granatum extract, pomegranate extract, herbal extracts, and any combination thereof.

It is another object of the invention to disclose a system as defined above, wherein said personalized oral care formulation includes at least two antimicrobial compounds or compositions in combination, said combination having a greater than additive in vitro antimicrobial effect than either of said two antimicrobial compounds provided separately under the same in vitro conditions.

It is another object of the invention to disclose a system as defined above, wherein said personalized oral care formulation includes at least two antimicrobial compounds or compositions in combination, said combination having a greater than additive in vitro antimicrobial effect than either of said two antimicrobial compounds provided separately under the same in vivo conditions.

It is thus one object of the present invention to disclose a method for providing a personalized oral care formulation for a patient comprising steps of obtaining a system comprising:
 a. a detection module for detecting characteristics of a bacterial oral infection;
 b. an in vitro test module for testing antibacterial activity of a panel of antimicrobial compounds;
 c. an oral care compounding module for receiving data from said in vitro test module concerning effectiveness of members of said panel on said antibacterial activity;
 d. wherein said oral care compounding module provides instructions on producing said oral care product containing an optimized selection of members of said panel of antimicrobial compounds; and
 e. operating said system to provide said personalized oral care formulation for said patient.

It is another object of the invention to disclose a method as defined above, wherein said oral care formulation is selected from the group comprising of an oral formulation is in the form of a mouthwash, dentifrice or toothpaste.

It is another object of the invention to disclose a method as defined above, wherein said panel of antimicrobial compounds or compositions, comprises cannabinoids, chlorhexidine compounds, chlorhexidine gluconate, cationic antimicrobial compounds, essential oils, fluoride compounds, chlamoxicillin, amoxicillin/clavulanate, clindamycin, metronidazole, punica granatum extract, pomegranate extract, herbal extracts or any combination thereof It is another object of the invention to disclose a method as defined above, wherein said oral care compounding module is operationally connected to an oral care formulation production line.

It is another object of the invention to disclose a method as defined above, wherein said system additionally comprises a database for storing output of patient results from detection module, in vitro test module or oral care compounding module or any combination thereof.

It is another object of the invention to disclose a method as defined above, wherein said system additionally comprises a server configured for processing and storing patients' medical and/or dental data.

It is another object of the invention to disclose a method as defined above, wherein said composition of an oral formulation is in the form of a mouthwash, dentifrice or toothpaste.

It is another object of the invention to disclose a method as defined above, wherein said panel of antimicrobial compounds or compositions is selected from a group consisting cannabinoids, cannabis related substances. THCA, CBDA, cannabinolic acid (CBNA), cannabigerolic acid (CBGA), cannabichromenic acid (CBCA) and cannabinodiolic acid (CBNDA) cannabinoids, chlorhexidine compounds, chlorhexidine gluconate, cationic antimicrobial compounds, essential oils, fluoride compounds, chlamoxicillin, amoxicillin/clavulanate, clindamycin, metronidazole or any combination thereof.

It is another object of the invention to disclose a method as defined above, wherein said cannabis related substances, comprise Dronabinol, Nabiximols, Nabilone, THC, CBD, Cannabidiol, LevonantradolAjulemic acid, (CT3), ECP002A, Natural Δ9-THC, Cannabichromenes, Cannabichromene (CBC), Cannabichromenic acid (CBCA), Cannabichromevarin (CBCV), Cannabichromevarinic acid (CBCVA), Cannabidiol Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoins, Cannabielsoic acid B (CBEA-B), Cannabielsoin (CBE), Cannabielsoin acid A (CBEA-A), Cannabigerols, Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA, Cannabinols and cannabinodiols, Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriols, 10-Ethoxy-9-hydroxy-delta-6a-tetrahydrocannabinol, 8,9-Dihydroxy-delta-6a-tetrahydrocannabinol, Cannabitriol (CBT), Cannabitriolvarin (CBTV), Delta-8-tetrahydrocannabinols, Delta-8-tetrahydrocannabinol ($\Delta^8$-THC), Delta-8-tetrahydrocannabinolic acid ($\Delta^8$-THCA), Delta-9-tetrahydrocannabinols, Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA) 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC), 3,4,5,6-Tetrahydro-7-hydroxy-alpha-alpha-2-trimethyl-9-n-propyl-2,6-methano-2H-1-benzoxocin-5-methanol, or OH-iso-HHCV or any combination thereof.

It is another object of the invention to disclose a method as defined above, wherein said personalized oral care formulation includes at least two antimicrobial compounds or compositions in combination, said combination having a greater than additive in vitro antimicrobial effect than either of said two antimicrobial compounds provided separately under the same in vitro conditions.

It is another object of the invention to disclose a method as defined above, wherein said personalized oral care formulation includes at least two antimicrobial compounds and compositions in combination, said combination having a greater than additive in vitro antimicrobial effect than either of said two antimicrobial compounds provided separately under the same in vivo conditions.

It is thus one object of the present invention to disclose a personalized oral care formulation for a patient comprising members of a predetermined panel of antimicrobial compounds or compositions, said antimicrobial compounds or compositions selected by:
  a. detecting characteristics of a bacterial oral infection;
  b. in vitro testing antibacterial activity of a panel of antimicrobial compounds;
  c. providing said oral care formulation by receiving data from said in vitro test module concerning effectiveness of members of said panel of antimicrobial compounds on said antibacterial activity and including members of said panel of antimicrobial compounds in said formulation according to optimized said data from said in vitro test module.

It is another object of the invention to disclose a formulation as defined above, wherein said panel of antimicrobial compounds or compositions selected from a group consisting cannabinoids, chlorhexidine compounds, chlorhexidine gluconate, cationic antimicrobial compounds, essential oils, fluoride compounds, chlamoxicillin, amoxicillin/clavulanate, clindamycin, metronidazole or any combination, punica granatum extract, pomegranate extract, herbal extracts thereof.

It is another object of the invention to disclose a formulation as defined above, wherein said panel of antimicrobial compounds or compositions, comprises THCA, CBDA, cannabinolic acid (CBNA), cannabigerolic acid (CBGA), cannabichromenic acid (CBCA) and cannabinodiolic acid (CBNDA) or any combination thereof.

It is another object of the invention to disclose a formulation as defined above, wherein said panel of antimicrobial compounds or cannabis related substance comprises Dronabinol (2), Nabiximols, Nabilone, THC, CBD, Cannabidiol, LevonantradolAjulemic acid, (CT3), ECP002A, Natural Δ9-THC, Cannabichromenes, Cannabichromene (CBC), Cannabichromenic acid (CBCA), Cannabichromevarin (CBCV), Cannabichromevarinic acid (CBCVA), Cannabidiol Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoins, Cannabielsoic acid B (CBEA-B), Cannabielsoin (CBE), Cannabielsoin acid A (CBEA-A), Cannabigerols, Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA, Cannabinols and cannabinodiols, Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriols, 10-Ethoxy-9-hydroxy-delta-6a-tetrahydrocannabinol, 8,9-Dihydroxy-delta-6a-tetrahydrocannabinol, Cannabitriol (CBT), Cannabitriolvarin (CBTV), Delta-8-tetrahydrocannabinols, Delta-8-tetrahydrocannabinol ($\Delta^8$-THC), Delta-8-tetrahydrocannabinolic acid ($\Delta^8$-THCA), Delta-9-tetrahydrocannabinols, Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA) 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC), 3,4,5,6-Tetrahydro-7-hydroxy-alpha-alpha-2-trimethyl-9-n-propyl-2,6-methano-2H-1-benzoxocin-5-methanol, or OH-iso-HHCV or any combination thereof.

It is another object of the invention to disclose a formulation as defined above, wherein said oral care formulation is selected from the group consisting of a mouthwash, dentifrice or toothpaste.

It is another object of the invention to disclose a formulation as defined above, wherein said personalized oral care formulation includes at least two antimicrobial compounds or compositions, in combination, said combination having a greater than additive in vitro antimicrobial effect than either of said two antimicrobial compounds or compositions, provided separately under the same in vitro conditions.

It is another object of the invention to disclose a formulation as defined above, wherein said personalized oral care formulation includes at least two antimicrobial compounds or compositions in combination, said combination having a greater than additive in vitro antimicrobial effect than either of said two antimicrobial compounds or compositions provided separately under the same in vivo conditions.

It is thus one object of the present invention to disclose an oral care compound cartridge configured to be operationally connected to an end user toothpaste package, dentifrice package or mouthwash container said cartridge characterized by:
  a. a chamber for holding an oral care compound comprising an antimicrobial compound;
  b. a mixing member for mixing said oral care compound with toothpaste extruded from a toothpaste or dentifrice tube;
  c. a coupling member for coupling to said toothpaste or dentifrice tube;
  d. an outlet for dispensing said toothpaste, said oral care compound is obtainable from a system comprising:
  e. a detection module for detecting characteristics of a bacterial oral infection;
  f. an in vitro test module for testing antibacterial activity of a panel of antimicrobial compounds or compositions;
  g. an oral care compounding module for receiving data from said in vitro test module concerning effectiveness of members of said panel on said antibacterial activity;
  wherein said oral care compounding module provides instructions on producing said oral care product containing an optimized selection of members of said panel of antimicrobial compounds or compositions and operation of said system provides said personalized oral care formulation for said patient.

It is another object of the invention to disclose an oral care compound cartridge as defined above, wherein said oral care formulation is selected from the group comprising of an oral formulation is in the form of a mouthwash, dentifrice or toothpaste It is another object of the invention to disclose an oral care compound cartridge as defined above, wherein said oral care compounding module is operationally connected to an oral care formulation production line.

It is another object of the invention to disclose an oral care compound cartridge as defined above, wherein said system additionally comprises a database for storing output of patient results from detection module, in vitro test module or oral care compounding module or any combination thereof.

It is another object of the invention to disclose an oral care compound cartridge as defined above, wherein said system additionally comprises a server configured for processing and storing patients' medical and/or dental data.

It is another object of the invention to disclose an oral care compound cartridge as defined above, wherein said composition of an oral formulation is in the form of a mouthwash, dentifrice or toothpaste.

It is another object of the invention to disclose an oral care compound cartridge as defined above, wherein said panel of antimicrobial compounds or compositions comprises cannabinoids, chlorhexidine compounds, chlorhexidine gluconate, cationic antimicrobial compounds, essential oils, fluoride compounds, chlamoxicillin, amoxicillin/clavulanate, clindamycin, metronidazole, punica granatum extract, pomegranate extract, herbal extracts or any combination thereof It is another object of the invention to disclose an oral care compound cartridge as defined above, wherein said panel of antimicrobial compounds or compositions comprises THCA, CBDA, cannabinolic acid (CBNA), cannabigerolic acid (CBGA), cannabichromenic acid (CBCA) and cannabinodiolic acid (CBNDA) or any combination thereof, Dronabinol (2), Nabiximols, Nabilone, THC, CBD, Cannabidiol, LevonantradolAjulemic acid, (CT3), ECP002A, Natural Δ9-THC, Cannabichromenes, Cannabichromene (CBC), Cannabichromenic acid (CBCA), Cannabichromevarin (CBCV), Cannabichromevarinic acid (CBCVA), Cannabidiol Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoins, Cannabielsoic acid B (CBEA-B), Cannabielsoin (CBE), Cannabielsoin acid A (CBEA-A), Cannabigerols, Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA, Cannabinols and cannabinodiols, Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriols, 10-Ethoxy-9-hydroxy-delta-6a-tetrahydrocannabinol, 8,9-Dihydroxy-delta-6a-tetrahydrocannabinol, Cannabitriol (CBT), Cannabitriolvarin (CBTV), Delta-8-tetrahydrocannabinols, Delta-8-tetrahydrocannabinol ($\Delta^8$-THC), Delta-8-tetrahydrocannabinolic acid ($\Delta^8$-THCA), Delta-9-tetrahydrocannabinols, Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA) 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC), 3,4,5,6-Tetrahydro-7-hydroxy-alpha-alpha-2-trimethyl-9-n-propyl-2,6-methano-2H-1-benzoxocin-5-methanol, or OH-iso-HHCV or any combination thereof.

It is another object of the invention to disclose an oral care compound cartridge as defined above, wherein said personalized oral care formulation includes at least two antimicrobial compounds or compositions in combination, said combination having a greater than additive in vitro antimicrobial effect than either of said two antimicrobial compounds or compositions provided separately under the same in vitro conditions.

It is another object of the invention to disclose an oral care compound cartridge as defined above, wherein said personalized oral care formulation includes at least two antimicrobial compounds or compositions in combination, said combination having a greater than additive in vitro antimicrobial effect than either of said two antimicrobial compounds or compositions provided separately under the same in vivo conditions.

It is thus one object of the present invention to disclose a personalized oral care formulation for a patient comprising members of a predetermined panel of antimicrobial compounds or compositions, said compounds are selected by:
  h. detecting characteristics of a bacterial oral infection;
  i. in vitro testing antibacterial activity of a panel of antimicrobial compounds; and
  j. providing said oral care formulation by receiving data from said In vitro test module concerning effectiveness of members of said panel of antimicrobial compounds on said antibacterial activity and including members of said panel of antimicrobial compounds in said formulation according to optimized said data from said in vitro test module.

It is another object of the invention to disclose a personalized oral care formulation as defined above, wherein said panel of antimicrobial compounds or compositions comprises of antimicrobial compounds comprises cannabinoids, chlorhexidine compounds, chlorhexidine gluconate, cationic antimicrobial compounds, essential oils, fluoride compounds, chlamoxicillin, amoxicillin/clavulanate, clindamycin, metronidazole, punica granatum extract, pomegranate extract, herbal extracts or any combination thereof.

It is another object of the invention to disclose a personalized oral care formulation as defined above, wherein said panel of antimicrobial compounds comprises of THCA, CBDA, cannabinolic acid (CBNA), cannabigerolic acid (CBGA), cannabichromenic acid (CBCA) and cannabinodiolic acid (CBNDA) or any combination thereof.

It is another object of the invention to disclose a personalized oral care formulation as defined above, wherein said panel of antimicrobial compounds or compositions, or cannabis related substances selected from a group consisting of Dronabinol (2), Nabiximols, Nabilone, THC, CBD, Cannabidiol, LevonantradolAjulemic acid, (CT3), ECP002A, Natural Δ9-THC, Cannabichromenes, Cannabichromene (CBC), Cannabichromenic acid (CBCA), Cannabichromevarin (CBCV), Cannabichromevarinic acid (CBCVA), Cannabidiol Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoins, Cannabielsoic acid B (CBEA-B), Cannabielsoin (CBE), Cannabielsoin acid A (CBEA-A), Cannabigerols, Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA, Cannabinols and cannabinodiols, Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriols, 10-Ethoxy-9-hydroxy-delta-6a-tetrahydrocannabinol, 8,9-Dihydroxy-delta-6a-tetrahydrocannabinol, Cannabitriol (CBT), Cannabitriolvarin (CBTV), Delta-8-tetrahydrocannabinols, Delta-8-tetrahydrocannabinol ($\Delta^8$-THC), Delta-8-tetrahydrocannabinolic acid ($\Delta^8$-THCA), Delta-9-tetrahydrocannabinols, Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA) 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC), 3,4,5,6-Tetrahydro-7-hydroxy-alpha-alpha-2-trimethyl-9-n-propyl-2,6-methano-2H-1-benzoxocin-5-methanol, or OH-iso-HHCV or any combination thereof.

It is another object of the invention to disclose a personalized oral care formulation as defined above, wherein said oral care formulation is selected from the group consisting of a mouthwash, dentifrice or toothpaste.

It is another object of the invention to disclose a personalized oral care formulation as defined above, wherein said personalized oral care formulation includes at least two antimicrobial compounds or compositions in combination, said combination having a greater than additive in vitro antimicrobial effect than either of said two antimicrobial compounds provided separately under the same in vitro conditions.

It is another object of the invention to disclose a personalized oral care formulation as defined above, wherein said personalized oral care formulation includes at least two antimicrobial compounds or compositions in combination, said combination having a greater than additive in vitro antimicrobial effect than either of said two antimicrobial compounds or compositions provided separately under the same in vivo conditions.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which.

DETAILED DESCRIPTION OF THE INVENTION

Figure 1:
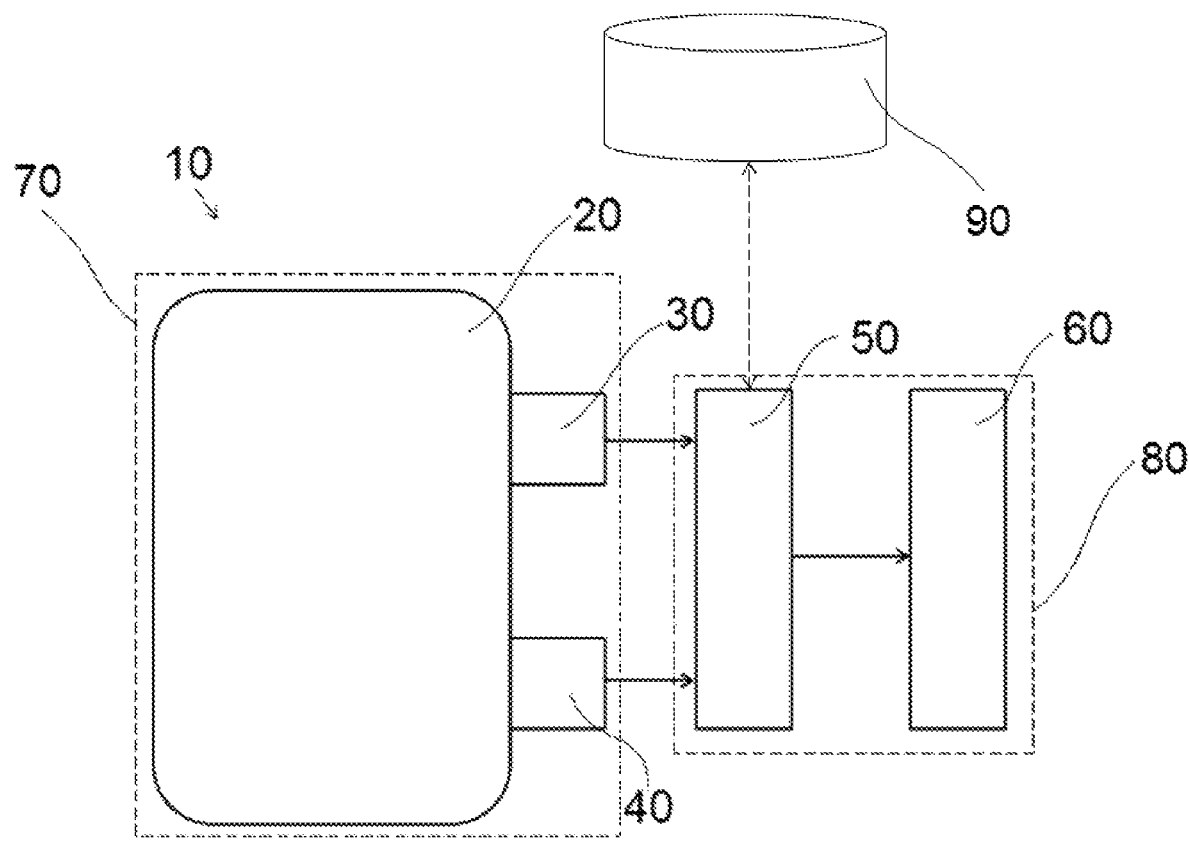
FIG. 1 is a schematic diagram of a system for detecting an intraoral disease and determining a treatment scheme.

The following description is provided, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide a system for detecting an intraoral disease and determining a treatment scheme and a method of doing the same.

The term periodontal (gum) disease refers hereinafter a plaque biofilm-induced inflammatory condition affecting tooth-supporting tissues and bone, and it is among humanity's most common diseases affecting up to 90% of the adult population worldwide Periodontal disease is also closely associated with non-communicable diseases as they share common risk factors (unhealthy diet, tobacco use, excessive alcohol consumption). It represents a major global oral disease burden with significant social, economic and health-system impacts. According to the FDI (world dental federation) 50% of worldwide population suffer from periodontal disease.

In its early stage, the periodontal disease is called gingivitis, the gums become swollen, red, and may bleed. In its more serious form, called periodontitis, the gums can pull away from the tooth, bone can be lost, and the teeth may loosen or fall out. Bad breath may also occur. Periodontal disease is generally due to bacteria in the mouth infecting the tissue around the teeth.

The term gingivitis refers hereinafter to s a non-destructive disease that causes inflammation of the gums. The most common form of gingivitis, and the most common form of periodontal disease overall, is in response to bacterial biofilms (also called plaque) that is attached to tooth surfaces, termed plaque-induced gingivitis. While some cases of gingivitis never progress to periodontitis, periodontitis is always preceded by gingivitis.

The terms oral bacterial flora, dental flora and oral flora refer hereinafter to the microorganisms (microbiota) of the oral cavity. The environment present in the human mouth allows the growth of characteristic microorganisms found there. It provides a source of water and nutrients, as well as a moderate temperature. Resident microbes of the mouth adhere to the teeth and gums to resist mechanical flushing from the mouth to stomach where acid-sensitive microbes are destroyed by hydrochloric acid. Anaerobic bacteria in the oral cavity include: *Actinomyces, Arachnia, Bacteroides, Bifidobacterium, Eubacterium, Fusobacterium, Lactobacillus, Leptotrichia, Peptococcus, Peptostreptococcus, Propionibacterium, Selenomonas, Treponema,* and *Veillonella.* Genera of fungi that are frequently found in the mouth include *Candida, Cladosporium, Aspergillus, Fusarium, Glomus, Alternaria, Penicillium,* and *Cryptococcus,* among others. Bacteria accumulate on both the hard and soft oral tissues in biofilms. Bacterial adhesion is particularly important for oral bacteria.

Some specific species of bacteria are believed to cause dental caries: *Streptococcus mutans* and *Lactobacillus* species among them. *Streptococcus mutans* are gram-positive bacteria which constitute biofilms on the surface of teeth. These organisms can produce high levels of lactic acid following fermentation of dietary sugars and are resistant to the adverse effects of low pH, properties essential for cariogenic bacteria. As the cementum of root surfaces is more easily demineralized than enamel surfaces, a wider variety of bacteria can cause root caries, including *Lactobacillus acidophilus, Actinomyces* spp., *Nocardia* spp., and *Streptococcus mutans.* Bacteria collect around the teeth and gums in a sticky, creamy-coloured mass called plaque, which serves as a biofilm. Some sites collect plaque more commonly than others, for example, sites with a low rate of salivary flow (molar fissures). Grooves on the occlusal surfaces of molar and premolar teeth provide microscopic retention sites for plaque bacteria, as do the interproximal sites. Plaque may also collect above or below the gingiva, where it is referred to as supra- or sub-gingival plaque, respectively.

The term dental plaque referees hereinafter to the material that adheres to the teeth and consists of bacterial cells (mainly *Streptococcus mutans* and *Streptococcus sanguis*), salivary polymers and bacterial extracellular products. Plaque is a biofilm on the surfaces of the teeth. This accumulation of microorganisms subject the teeth and gingival tissues to high concentrations of bacterial metabolites which results in dental disease. If not taken care of, the plaque can turn into tartar (its hardened form) and lead to gingivitis or periodontal disease.

The terms dental caries, tooth decay or dental cavities, refers to a breakdown of teeth due to acids made by bacteria. The cavities may be a number of different colors from yellow to black. Symptoms may include pain and difficulty with eating. Complications may include inflammation of the tissue around the tooth, tooth loss, and infection or abscess formation.

The terms halitosis or bad breath refer hereinafter to a symptom in which a noticeably unpleasant breath odour is present. In about 90% of genuine halitosis cases, the origin of the odor is in the mouth itself. This is known as intra-oral halitosis, oral malodor or oral halitosis.

The most common causes are odor producing biofilm on the back of the tongue, below the gum line, and in the pockets created by gum disease between teeth and the gums. This biofilm results in the production of high levels of foul odors. The odors are produced mainly due to the breakdown of proteins into individual amino acids, followed by the further breakdown of certain amino acids to produce detectable foul gases. Volatile sulfur compounds are associated with oral malodor levels, and usually decrease following successful treatment. Other parts of the mouth may also contribute to the overall odor, but are not as common as the back of the tongue. These locations are, in order of descending prevalence, inter-dental and sub-gingival niches, faulty dental work, food-impaction areas in between the teeth, abscesses, and unclean dentures. Oral based lesions caused by viral infections like herpes simplex and HPV may also contribute to bad breath.

The intensity of bad breath may differ during the day, due to eating certain foods (such as garlic, onions, meat, fish, and cheese), smoking, and alcohol consumption. Since the mouth is exposed to less oxygen and is inactive during the night, the odor is usually worse upon awakening ("morning breath"). Bad breath may be transient, often disappearing following eating, drinking, tooth brushing, flossing, or rinsing with specialized mouthwash. Bad breath may also be persistent (chronic bad breath), which affects some 25% of the population in varying degrees.

The term Allelopathy refers hereinafter to a biological phenomenon by which an organism produces one or more biochemicals that influence the germination, growth, survival, and reproduction of other organisms. These biochemicals are known as allelochemicals and can have beneficial (positive allelopathy) or detrimental (negative allelopathy) effects on the target organisms and the community. Allelochemicals are a subset of secondary metabolites which are not required for metabolism (i.e. growth, development and reproduction) of the allelopathic organism. Allelochemicals with negative allelopathic effects are an important part of plant defense against herbivory.

The present invention will chiefly benefit patients suffering from or at risk of dental caries or halitosis.

The present invention provides a system and method for supplying individual patients with customized personal oral care products wherein the products (mouthwashes, dentifrices, toothpastes and the like) are produced using the following process; (i) characterization of disease causing bacteria in the individual patient (ii) in vitro testing of the disease causing bacteria by antimicrobial compounds preferably, but not only, cannabinoids (iii) compounding personalized products (mouthwashes, dentifrices, toothpastes and the like) by exploiting the results of (i) and (ii) to provide personalized products.

It is herein acknowledged that the present invention provides a system for customizing oral care preparations such as mouthwashes, dentifrices and toothpastes that will be compounded for and delivered to the individual patient on the basis of an optimized formulation for treatment of caries best suited for the individual patient in need. It is further acknowledged that the aforementioned oral care preparations will be formulated with materials comprising cannabinoids as well as the more conventional constituents of oral preparations.

It is herein acknowledged that the present invention includes an oral care compound cartridge containing an optimized selection of members of a predetermined panel of antimicrobial compounds. The oral care compound cartridge is configured to be operationally connected to an end user toothpaste package, dentifrice package or mouthwash container.

It is herein acknowledged that it is within the scope of the present invention to provide the panel of antimicrobial compounds denoted below whether produced naturally from the plant, algal, animal, bacterial or fungal organism or synthetic analogues or derivatives thereof.

It is herein acknowledged that the panel of antimicrobial compounds comprises cannabinoids, chlorhexidine compounds, chlorhexidine gluconate, cationic antimicrobial compounds, essential oils, fluoride compounds, chlamoxicillin, amoxicillin/clavulanate, clindamycin, metronidazole, or any combination thereof.

It is further herein acknowledged that the panel of antimicrobial compounds comprises cannabinoids THCA, CBDA, cannabinolic acid (CBNA), cannabigerolic acid (CBGA), cannabichromenic acid (CBCA) and cannabinodiolic acid (CBNDA) or any combination thereof.

It is further herein defined that the panel of antimicrobial compounds of the system, methods and various products of the present invention panel comprises cannabis related substance selected from the group consisting of Dronabinol (2), Nabiximols, Nabilone, THC, CBD, Cannabidiol, Levonantradol Ajulemic acid, (CT3), ECP002A, Natural Δ9-THC, Cannabichromenes, Cannabichromene (CBC), Cannabichromenic acid (CBCA), Cannabichromevarin (CBCV), Cannabichromevarinic acid (CBCVA), Cannabidiol Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoins, Cannabielsoic acid B (CBEA-B), Cannabielsoin (CBE), Cannabielsoin acid A (CBEA-A), Cannabigerols, Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA, Cannabinols and cannabinodiols, Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriols, 10-Ethoxy-9-hydroxy-delta-6a-tetrahydrocannabinol, 8,9-Dihydroxy-delta-6a-tetrahydrocannabinol, Cannabitriol (CBT), Cannabitriolvarin (CBTV), Delta-8-tetrahydrocannabinols, Delta-8-tetrahydrocannabinol ($\Delta^8$-THC), Delta-8-tetrahydrocannabinolic acid ($\Delta^8$-THCA), Delta-9-tetrahydrocannabinols, Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA) 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC), 3,4,5, 6-Tetrahydro-7-hydroxy-alpha-alpha-2-trimethyl-9-n-propyl-2,6-methano-2H-1-benzoxocin-5-methanol, or OH-iso-HHCV or any combination thereof.

It is further herein acknowledged that the panel of antimicrobial compounds comprises chlorhexidine compounds, chlorhexidine gluconate, cationic antimicrobial compounds, essential oils, fluoride compounds, chlamoxicillin, amoxicillin/clavulanate, clindamycin, metronidazole, punica granatum extract, pomegranate extract, herbal extracts.

It is further herein acknowledged that the panel of antimicrobial compounds comprises antibacterial compounds derived from marine organisms including the following organisms macro and microalgae, cnidarians, phytoplankton, molluscs, sponges, corals, tunicates, and bryozoans.

It is further herein acknowledged that the panel of antimicrobial compounds comprises antibacterial compounds derived from Phaeophyceae (brown), Rhodophyceae (red), Chlorophyceae (green), Chrysophyceae (golden) and Bacillariophyceae (diatoms).

It is further herein acknowledged that the panel of antimicrobial compounds comprises antibacterial compounds derived from lobophorenols ($C_{21}$ polyunsaturated alcohols) in the brown seaweed genus, *Lobophora*, acetylated diterpenes produced from green alga, *Chlorodesmis fastigiata*, two loliolide derivatives from the red alga, *Galaxaura filamentosa*, kainic acid and/or its analogue, domoic acid, from the diatom genus, *Pseudonitzschia*, ovatoxins and palytoxins isolated from dinoflagellate protozoan, *Ostreopsis*, extracts of *Caulerpa cylindracea* and any naturally produced or synthetic allelochemical.

It is further herein acknowledged that the panel of antimicrobial compounds comprises Functional groups with antibacterial activity selected from the group consisting of phlorotannins, fatty acids, polysaccharides, peptides, terpenes, polyacetylenes, sterols, indole alkaloids, aromatic organic acids, shikimic acid, polyketides, hydroquinones, alcohols, aldehydes, ketones, and halogenated furanones, alkanes, and alkenes.

It is further acknowledged that the abovementioned antimicrobial compounds are selected for inclusion into the individual patient's customized oral preparation by steps of
a. Collecting a sample of a biologic material from an oral cavity of a patient
b. detecting characteristics of dental flora or bacterial oral infection
c. testing in vitro antibacterial activity of a panel of antimicrobial compounds on the dental flora or bacterial oral infection
d. receiving data from said in-vitro test module concerning effectiveness of members of said panel on said antibacterial activity
e. compounding said oral care product containing an optimized selection of members of said panel of antimicrobial compounds.

optionally providing the optimized selection of members of the panel of antimicrobial compounds within an oral care compound cartridge configured to be operationally connected to an end users toothpaste package, dentifrice package or mouthwash container.

Example 1

Reference is now made to FIG. 1 presenting system 10 for detecting an intraoral disease and determining a treatment scheme for an individual patient (personalized treatment in dentistry). According to one embodiment of the present invention, system 10 is implemented on the basis of a "Lab-on-a-chip" solution. Specifically, the system includes two main parts 70 and 80. Part 70 constitutes a mechanical arrangement comprises reservoir 20 for placement of a sample of biological material collected from an intraoral cavity. Numerals 20 and 30 refer to a first sensor configured for first detection assay for detecting a first substance originating from bacteria and a second sensor for carrying out a second detection assay for detecting a second substance originating from at least one of an immune and an inflammatory system of the patient, respectively. According to the present invention, part 70 is integrally embodied.

Signals transmitted by sensors 20 and 30 are received by control unit 50 where the signals are processed and analyzed. Second main part 80 includes control unit 50 which is configured for correlative analysis of the obtained signals from sensors 20 and 30 and determining a treatment scheme. Then, the determined treatment scheme is displayed by display means 60. It is important from the practical point of view to note that, control unit 50 and display means 60 can be embodied on the basis of a smartphone or similar computer means when its processor, display and application program are used.

According to one embodiment of the present invention, the treatment scheme comprises a type of relevant cannabinoid and its dosing frequency.

According to other embodiments of the present invention, the system comprises a server 90 and a plurality of end user's devices configured for detecting an intraoral disease and determining a treatment scheme. Server 90 functions as a processing and data storing means generalizing medical statistics concerning the intraoral disease.

Figure 2:
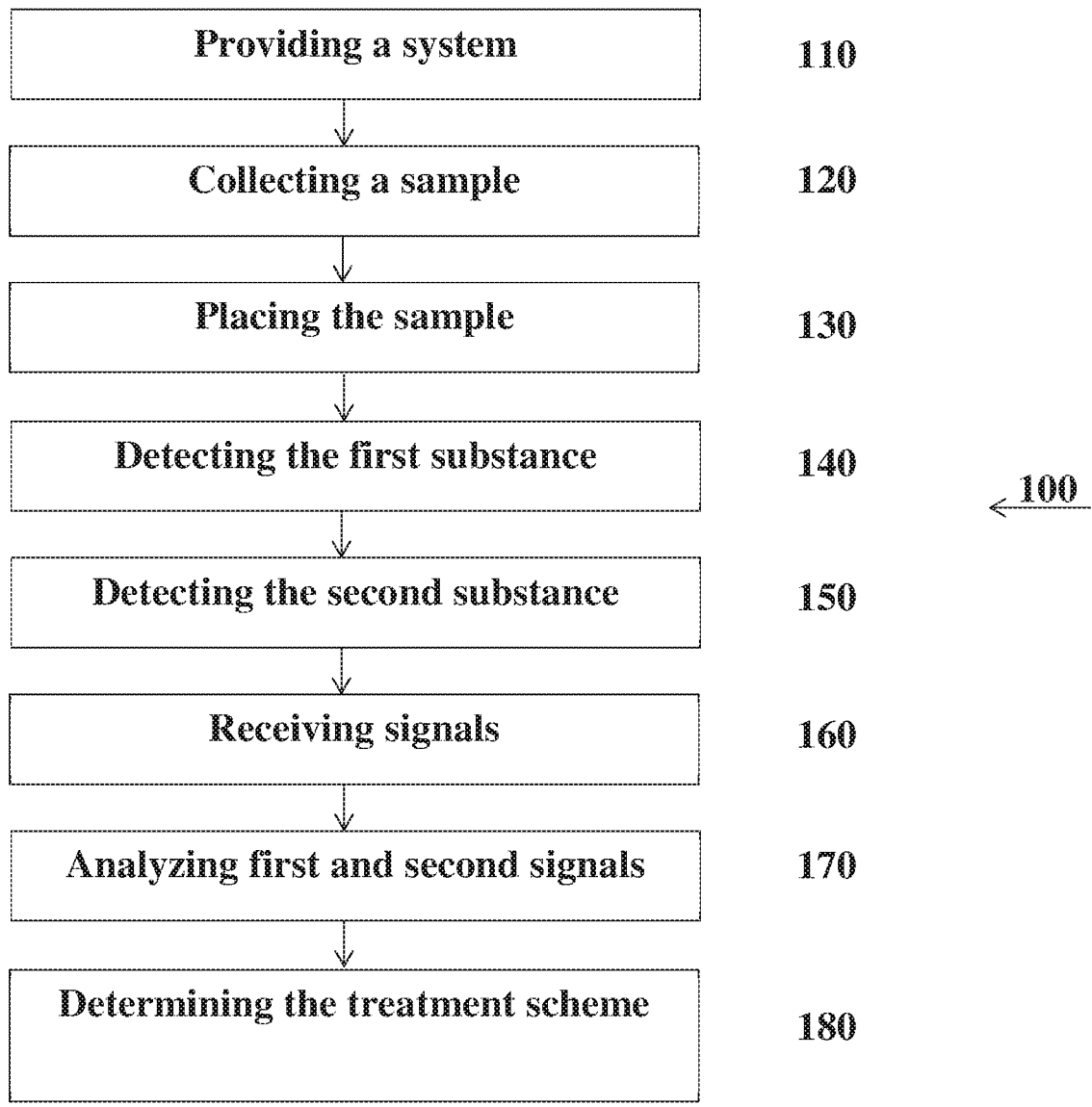
FIG. 2 is a flowchart of a method of detecting an intraoral disease and determining a personalized treatment scheme.

Reference is now made to FIG. 2 presenting method 100 of detecting an intraoral disease and determining a treatment scheme. After providing a system detecting an intraoral disease and determining a treatment scheme at step 110, collecting a sample of biologic material from said oral cavity of said patient is carried out (step 120). The sample of the biologic material is placed into the reservoir (step 130). The first detection assay for detecting a first substance originating from bacteria by the first sensor and the second detection assay for detecting a second substance originating from at least one of an immune and an inflammatory system of the patient by the second sensor are carried out at steps 140 and 150, respectively.

The control unit receives signals from the first and second sensors (steps 160). After correlatively analyzing the obtained signals (step 170), the treatment scheme is determined. According to one embodiment of the present invention, the treatment scheme includes a type of relevant antimicrobial compound and its dosing frequency (180).

According to the present invention, a system for detecting an intraoral disease and determining a treatment scheme is disclosed. The aforesaid system comprises: (a) a reservoir configured for accommodating a sample of a biologic material collected in an oral cavity of a patient; (b) a first detector for detecting a first substance originating from bacteria; (c) a second detector for detecting a second substance originating from at least one of an immune and an inflammatory system of the patient; and (d) a control unit configured for operatively receiving signals from the first and second detectors and analyzing the signals.

It is a core feature of the invention to provide the control unit configured for determining the treatment scheme comprising a type of relevant cannabinoid and a dosing frequency thereof.

According to one embodiment of the present invention, the system comprises means for collecting the sample of a biologic material from the patient's oral cavity.

According to a further embodiment of the present invention, the system comprises means for collecting the sample of a biologic material from the patient's CEJ—Cement Enamel Junction, collected by consumer/dentist professionals.

According to a further embodiment of the present invention, the system comprises means for collecting the sample of a biologic material from the patient's dentinal interprismatic fluid to be analyzed by the present invention and indicate the best suitable antibacterial application According to a further embodiment of the present invention, the system comprises means for collecting the sample of a biologic material from the patient's intracanal fluids for detection of the best suitable antibacterial, application According to a further embodiment of the present invention, the system comprises means for collecting the sample of a biologic material from the patient's intrabone fluids collected by dental professionals for detection of the best suitable antibacterial, application According to a further embodiment of the present invention, the reservoir, the first detector and the second detector are arranged into an integral part connectable to computer means selected from the group consisting of a desktop computer, a laptop computer, a tablet, a smartphone and any combination thereof having a nontransitive computer-readable medium comprising commands for analyzing said signals and determining said treatment scheme.

According to further embodiment of the present invention, the first substance is a bacterial virulence product.

According to a further embodiment of the present invention, the first substance is an enzyme.

According to a further embodiment of the present invention, the enzyme is a protease.

According to a further embodiment of the present invention, protease is selected from the group consisting of arg-gingipain from *Porphyromonas gingivalis* and a 48 kDa protease from *Bacteroides forsythus*.

According to a further embodiment of the present invention, the first substance is a toxin.

A further object of the invention is to disclose the toxin which is a leukotoxin from *Actinobacillus actinomycetemcomitans*.

A further object of the invention is to disclose the second substance which is a leukocyte product.

According to a further embodiment of the present invention, the leukocyte product is a natural serine protease.

According to a further embodiment of the present invention, the natural serine protease is a human neutrophil elastase.

According to a further embodiment of the present invention, the second substance is a cytokine.

A further object of the invention is to disclose the cytokine which is an interleukin.

According to a further embodiment of the present invention, the interleukin is chosen from among interleukin-1β, interleukin-6 and interleukin-8.

According to a further embodiment of the present invention, the cytokine is an inflammatory mediator.

According to a further embodiment of the present invention, the inflammatory mediator is selected from the group consisting of tumour necrosis factor-α and prostaglandin $E_2$.

Example 2

According to a further embodiment of the present invention, the system for detecting an intraoral disease and determining a treatment scheme is disclosed. The aforesaid system comprises: (a) a server configured for processing and storing patients' medical data; (b) a plurality of devices for detecting an intraoral disease; each device comprising: (i) a reservoir configured for accommodating a sample of a biologic material collected in an oral cavity of a patient; (ii) a first detector for detecting a first substance originating from bacteria; (iii) a second detector for detecting a second substance originating from at least one of an immune and an inflammatory system of the patient; (iv) a control unit configured for operatively receiving signals from the first and second detectors and analyzing the signals; (v) display means configured for presenting results of signal analysis. The server is configured for determining said treatment scheme comprising a type of relevant cannabinoid and a dosing frequency thereof.

According to a further embodiment of the present invention a method of detecting an intraoral disease and determining a treatment scheme is disclosed. The aforesaid method comprises steps: (a) providing a system for detecting a intraoral disease and determining a treatment scheme; the system comprising: (i) a reservoir configured for accommodating a sample of a biologic material collected in an oral cavity of a patient; (ii) a first detector for detecting a first substance originating from bacteria; (iii) a second detector for detecting a second substance originating from at least one of an immune and an inflammatory system of the patient; and (iv) a control unit configured for operatively receiving signals from the first and second detectors and analyzing the signals; control unit is configured for determining the treatment scheme comprising a type of relevant cannabinoid and a dosing frequency thereof; (b) collecting a sample of biologic material from the oral cavity of the patient; (c) placing the sample of biologic material into the reservoir; (d) detecting the first substance within the sample of biologic material; (e) detecting the second substance within the sample of biologic material; (f) receiving signals from the first and second detectors; (g) analyzing the first and second signals in a correlational manner; and (h) determining the treatment scheme comprising a type of relevant cannabinoid and a dosing frequency thereof.

Example 3

Figure 3:
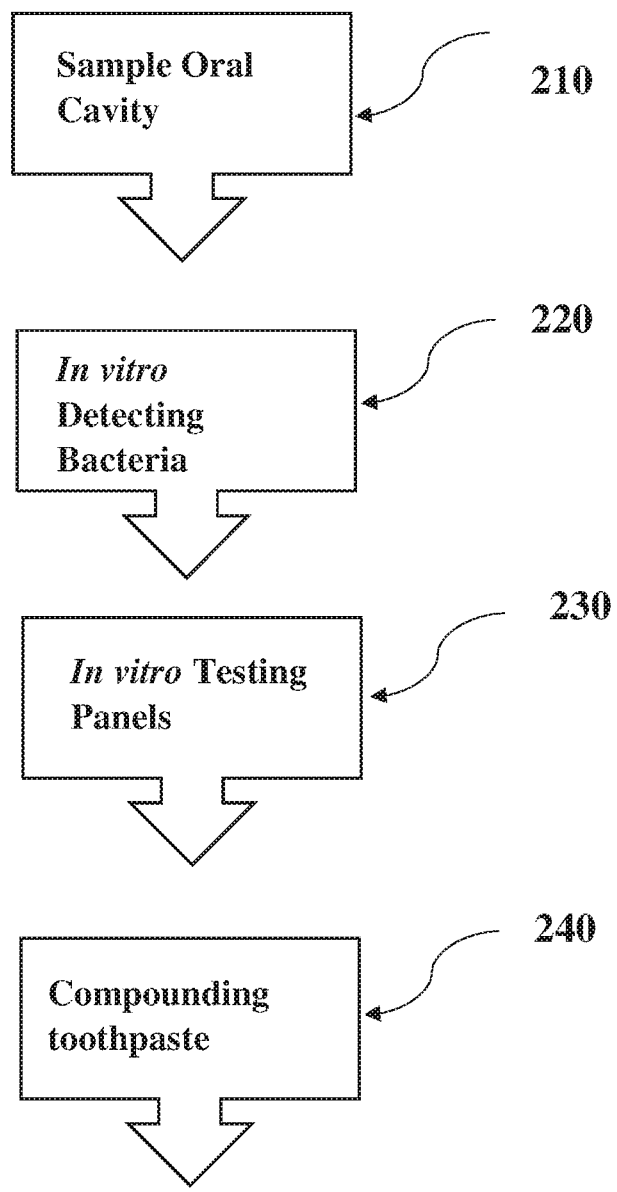
FIG. 3 is a flowchart of a method for compounding toothpaste for patient by sampling an oral cavity.

FIG. 3 provides an example of the features of the present invention:

Oral bacteria are sampled from an individual patient oral cavity 210. In vitro detection of the sampled bacteria is carried out 220. The bacteria are subjected to the testing panels of the present invention, comprising cannabinoids 230. The personalized toothpaste incorporating the best cannabinoid panel is formulated according to the data from 230.

Example 4

Figure 4:
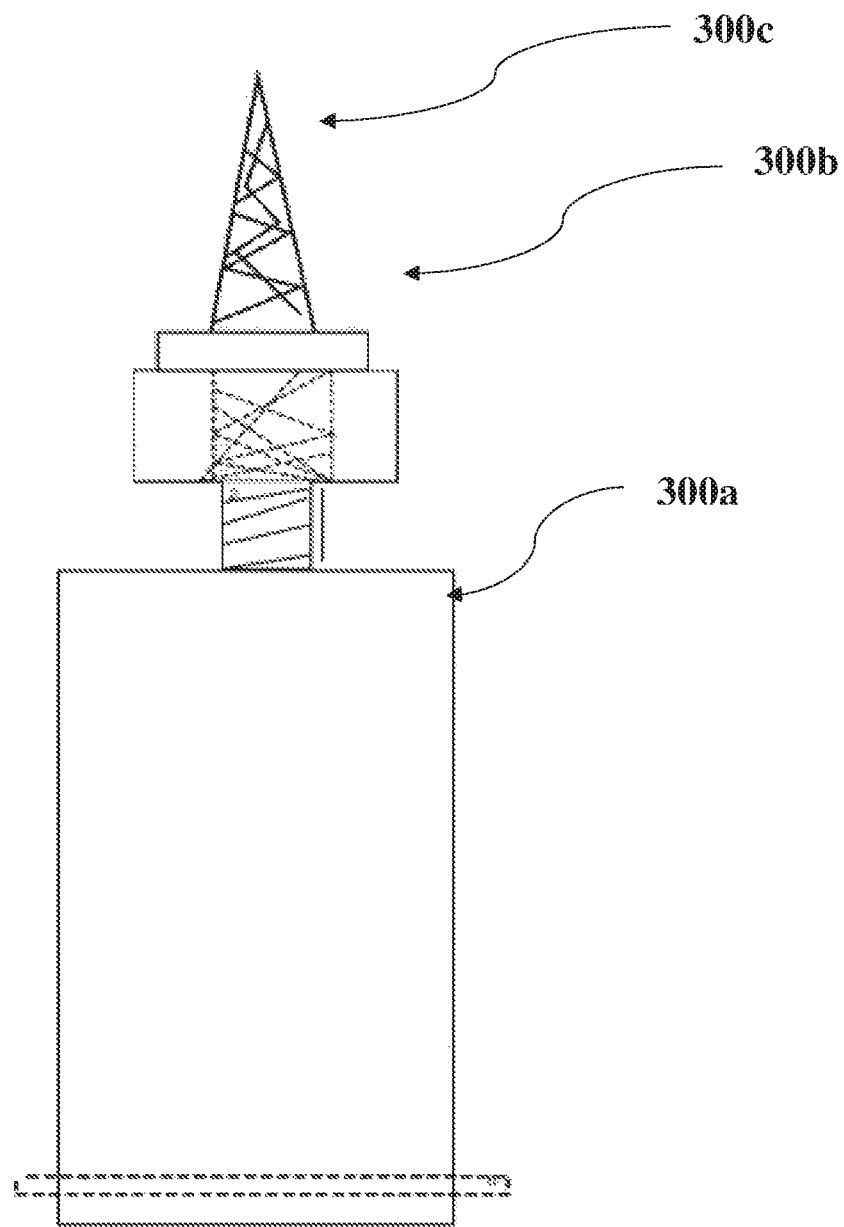
FIG. 4 is an illustration of an oral care compound cartridge.

FIG. 4 illustrates a non-limiting embodiment of the present invention:

An oral care compound cartridge is configured to be operationally connected to an end user toothpaste package, dentifrice package or mouthwash container. The cartridge is characterized by
 a. A chamber for holding an oral care compound
 b. A mixing member for mixing said oral care compound with toothpaste extruded from a toothpaste or dentifrice tube
 c. A coupling member and outlet for coupling to said toothpaste or dentifrice tube (not shown).

It is acknowledged herein that embodiments of the oral care cartridge of the present invention are adapted for use with mouthwash bottles and dispensers.

It is further acknowledged herein that embodiments of the present invention include said oral care compounds obtainable from a system comprising:
 a. a detection module for detecting characteristics of a bacterial oral infection
 b. an in vitro test module for testing antibacterial activity of a panel of antimicrobial compounds.
 c. an oral care compounding module for receiving data from said in vitro test module concerning effectiveness of members of said panel on said antibacterial activity
wherein said oral care compounding module provides instructions on producing said oral care product containing an optimized selection of members of said panel of antimicrobial compounds and operation of said system provides said personalized oral care formulation for said patient.

It is herein acknowledged that the antimicrobial compounds of embodiments of the present invention include in a non-limiting manner:
cannabinoids, chlorhexidine compounds, chlorhexidine gluconate, cationic antimicrobial compounds, essential oils, fluoride compounds, chlamoxicillin, amoxicillin/clavulanate, clindamycin, metronidazole, punica granatum extract, pomegranate extract, herbal extracts and any combination thereof.

Example 5

Methods of the present invention are hereby exemplified. The trial included two stages:
a. Stage 1: In vitro determination of sensitivity of dental biofilm flora from individual patients to cannabinoid test panels.
b. Stage 2: Effectiveness of toothpaste compounded to individual patient's best cannabinoid panel formulations.

Stage 1: In Vitro Determination of Sensitivity of Dental Biofilm Flora from Individual Patients to Cannabinoid Test Panels.

Ten (10) subjects (patients A-J) were involved in the trial. Dental biofilm was collected of these subjects by means of swabs, scrapes and other devices. The bacteria of this dental biofilm were characterized by conventional methods such as growth on selective media, microscopic examination and lab on-chip-laser analysis (e.g. Parochip).

Patient's bacteria from patients A-J were tested in vitro on substrates seeded with a panel of cannabinoids as illustrated in table 1 below:

TABLE 1

The in vitro effectiveness of cannabinoids on dental bacteria taken from various patients.

|   | A | B | C | D | E | F | G | H | I | J |
|---|---|---|---|---|---|---|---|---|---|---|
| 1 | ++ | +++++ | ++++ | + | +++ | − | +++++ | ++ | − | − |
| 2 | + | ++++ | − | ++ | ++++ | +++ | − | − | ++++ | ++ |
| 3 | +++ | − | + | + | − | − | ++++ | ++ | +++ | − |
| 4 | + | +++ | +++++ | ++++ | ++++ | ++++ | ++++ | ++ | ++++ | ++ |
| 5 | ++++ | − | +++ | ++++ | +++ | ++ | ++ | +++++ | ++++ | ++ |
| 6 | ++ | ++ | + | ++ | − | − | +++ | + | ++ | − |
| 7 | − | − | − | − | − | − | − | − | − | − |

Key for Table 1:
Upper row: Oral flora samples collected from individual patients designated A-J
Left column: Panel of Cannabinoids being tested designated 1-7
The panel of cannabinoids was selected from: CBDA, cannabinolic acid (CBNA), cannabigerolic acid (CBGA), cannabichromenic acid (CBCA) and cannabinodiolic acid (CBNDA).

Column Panels:
1=CBDA;
2=CBDA+CBNA;
3=CBDA+CBNA+CBGA;
4=CBDA+CBNA+CBGA+CBCA;
5=CBDA+CBNA+CBGA+CBCA+CBNDA;
6=Chlorohexadine control, and
7=control with no antiseptic.

Results of in vitro testing are defined in terms of efficacy of panel cannabinoids in in vitro suppressing oral flora, in increasing scale of:

−, +, ++, +++, ++++, +++++

The results show that different patients have mouth flora with different sensitivities to cannabinoid panels. For example, panel 4=CBDA+CBNA+CBGA+CBCA is effective against the flora of patient C, and less effective against patient B and H. Panel 5=CBDA+CBNA+CBGA+CBCA+CBNDA was effective against flora of patient H, and Panel 1=CBDA was effective against flora of B.

Note that, in this particular trial, the results do not show predictability or demonstrate a synergistic effect of panels comprising a plurality of cannabinoids. This unpredictability demonstrates the utility of the method in being able to provide an appropriate cannabinoid component to a particular patient.

Stage 2 Effectiveness of Toothpaste Compounded to Individual Patient's Best Cannabinoid Panel Formulations.

Toothpastes were formulated according to the individual patient's best cannabinoid panel from stage 1. A 6 week trial was carried out as described in the aforementioned paragraphs:

Starting the first 3 weeks, patients used toothpastes of the aforementioned formulation 1 and formulation 2, with no added cannabinoids, and their dental flora were collected and characterized in quantity and species by methods described in the above-mentioned stage I.

During the subsequent 3 weeks, the patients used toothpastes of the aforementioned formulation 1 and formulation 2, with added cannabinoids, customized according to the results from the cannabinoid sensitivity determinations of stage 1, and their dental flora were collected and characterized in quantity and species by methods described in the above-mentioned stage I.

TABLE 2

The effectiveness of cannabinoids on dental bacteria of various patients.

| A | B | C | D | E | F | G | H | I | J |
|---|---|---|---|---|---|---|---|---|---|
| 5 | 1 | 4 | 4 | 2 | 4 | 1 | 5 | 2 | 2 |
| + | ++++ | − | ++ | ++++ | +++ | − | − | ++++ | ++ |

Key for Table 2:
Upper row: Oral flora samples collected from individual patients designated A-J;
The numbers refer to Panel of Cannabinoids beine tested designated 1-2, 4-5.
Results of in vitro testing are defined in terms of efficacy of panel cannabinoids in in vitro suppressing oral flora, in increasing scale of:
−, +, ++, +++, ++++, +++++

The dental flora were collected and characterized in quantity and species and results were scored. All customized patient/toothpaste panel combinations gave similar dental flora results as were reported by the in vitro testing.

TABLE 3

| Formulation 1: Toothpaste containing 1.5% CBD | | |
|---|---|---|
| Humectants 40-70% | Water 0-50% | Buffers/salts/tartar control 0.5-10 |
| Dead see Mud 40% | distilled water 20% | dead sea salt crystal 0.2 nm 0.5% |
| Organic thickeners (gums) 0.4-2 | Inorganic thickeners 0-12 | Abrasives 10-50 |
| | | Sodium bicarbonate 10% |
| Actives/Antibacterial agent 0.2-1.5 | Surfactants 0.5-2 | Flavor and sweetener 0.8-1 |
| CBD 1.5% | Cellulose ethers 0.5% | mint flavor 0.8% |

TABLE 4

| Formulation 2: Toothpaste containing 15% CBD | | |
|---|---|---|
| Humectants 40-70% | Water 0-50% | Buffers/salts/tartar control 0.5-10 |
| Dead see Mud 40% | distilled water 20% | dead sea salt crystal 0.2 nm 0.5% |
| Organic thickeners (gums) 0.4-2 | | |
| citric acid 1.5% | Inorganic thickeners 0-12 | Abrasives 10-50 |
| | | Sodium bicarbonate 10% |
| Actives/Antibacterial agent 0.2-1.5 | Surfactants 0.5-2 | Flavor and sweetener 0.8-1 |
| CBD 15% | Cellulose ethers 0.5% | mint flavor 0.8% |

Figure 5:
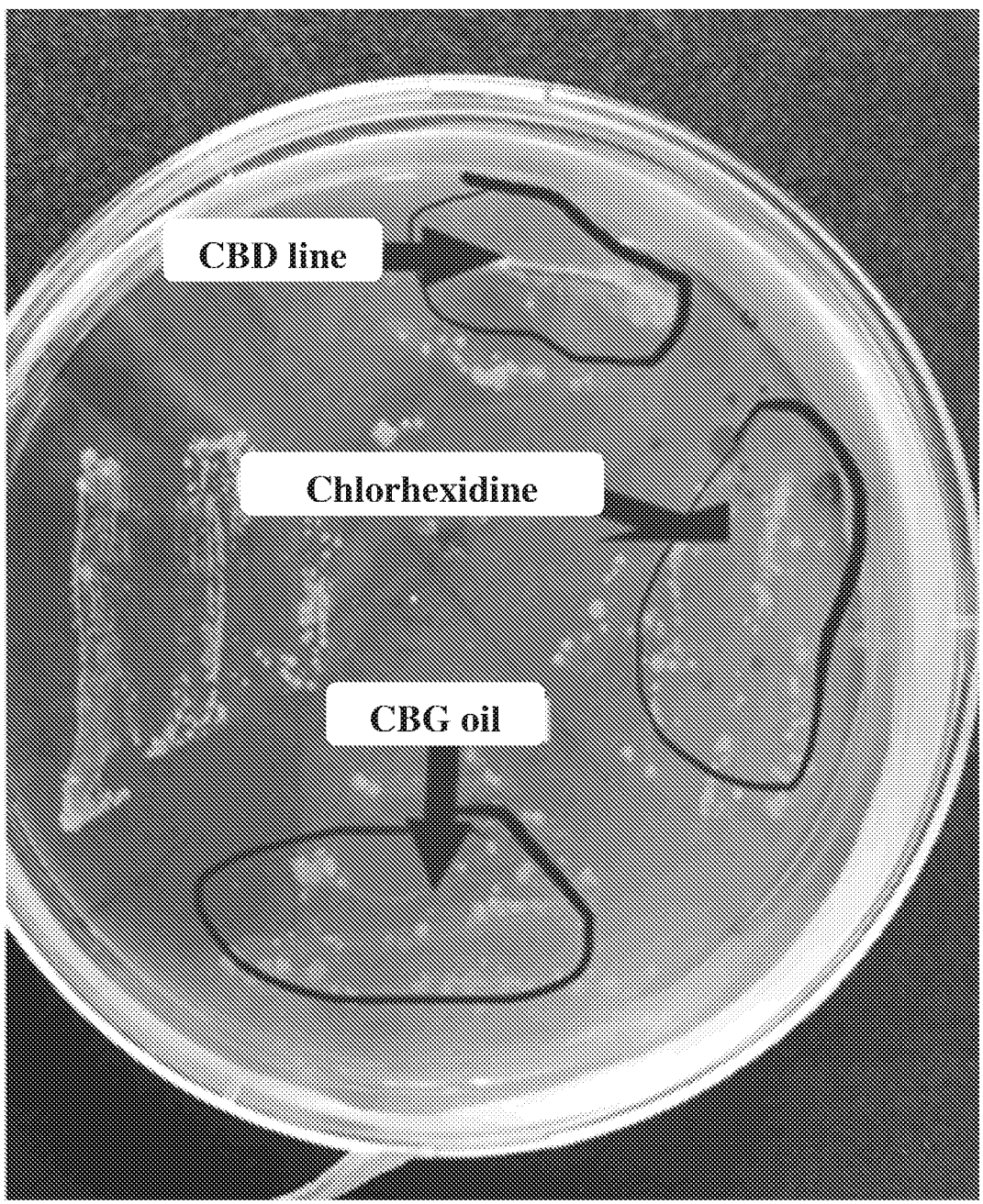
FIG. 5 is a photograph a culture of dental plaque microbes following 2 days incubation.

FIG. 5 shows a Culture of dental plaque microbes, following 2 days of incubation.

Streak of CBD applied to inoculum shows no bacterial growth.

Streak of Chlorhexidine applied to inoculum shows bacterial growth

Streak of CBG applied to inoculum bacterial growth

These results indicate in vitro effectiveness of CBD against dental plaque microbes.

Example 6

Reference is now made to an embodiment of the present invention disclosing the system mentioned above, said system offers personalized treatments recommended for a variety of periodontal and dental system diseases diagnosed by the system of the current invention.

This study evaluates different extracts/compounds on different types of human oral biofilms that normally are plaque-generating, further inducing light to severe periodontal diseases, as scored by DPSI (Dutch periodontic screening index).

The aim is to establish a repeated methodology that will assess efficacy of the treatment compounds, such as cannabis extracts measured on consumer's (patient's) oral sample, in order to reduce the bacterial live and aggressiveness potential, and establish a recommendation of possible extracts for oral health care products.

The objectives of this study are:
a. establishing a repeated methodology, that will assess efficacy of the compounds, in order to reduce the bacterial live circle and aggressiveness potential;
b. establishing a recommendation of possible extracts for oral health care products as addition to the daily used forms (toothpaste, mouthwash, oral spray);
c. recommending the consumer regarding the possibilities of reducing bacteria of his dental plaque; and
d. recommending the cannabis growers (growers A-D) regarding the potential of development of the selected oral health product additives with high healing potential, and a new income strain for the growers and dispensaries.

Summary: The method includes:
a. randomized sampling of oral plaque biofilm from different consumers with 0-+4 DPSI, dental pulp extraction with chronic pulpitis;
b. cultivation of the samples in incubator with 37° C., for 1 day. The colonies underwent treatment with different types of compounds CBC, CBD, CBG, CBGA, CBN for 5 minutes;
c. staining with fluorescent special dyes for live bacterial cells, following the cannabinoid compounds' treatment and using one referral without cannabinoids treatment;
d. mounting on 6 channel micro slide dishes with 0.1 high;
e. imaging with Cytetion 5 Biotek microscope on 40 magnification, analyzing and running live cell counting.

Conclusions: On dental plaque a reduction of 95% from the live bacterial cells was detected following treatment with CBGA, while on the dental pulp tissue a reduction of 92% was detected following CBD treatment. The other compounds reduced live bacterial cells levels to 60-85%. It is also concluded that on dental plaque from consumer A, the extract from Cannabis CBGA grower A was most efficient in comparison with CBGA compared to grower B.

Figure 6:
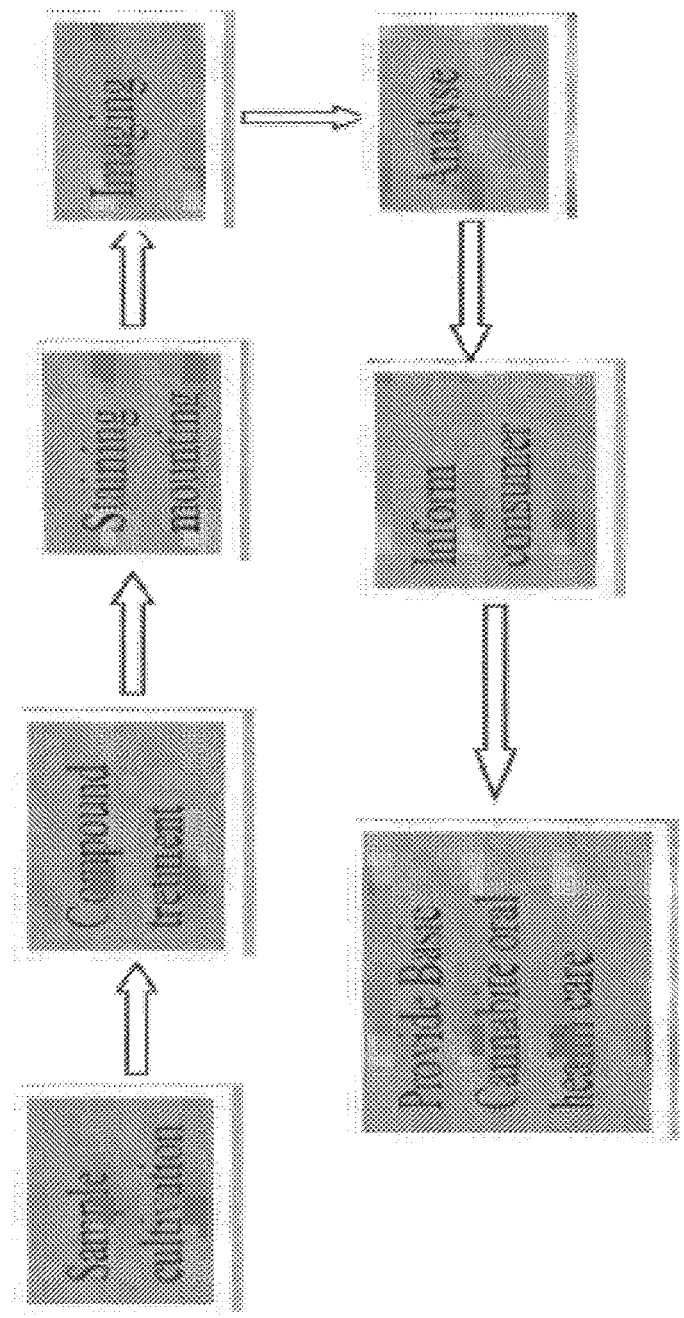
FIG. 6 is a flowchart of the steps of the methods used for detecting the effectiveness of various cannabinoids on personal oral plaque samples and recommending personalized cannabinoid oral health care.

Experimental methods: FIG. 6 depicts the steps of the methodology used in this protocol. The methodology includes the following steps:
a. Sample cultivation: Samples are collected with Flexi Grip 1702 Paro interdental brush. Cultivation on AGAR Petri Dish 100/15 mm incubated for 24 hours in 37° C.
b. Compound Treatment: The colonies are treated with 25%, 12.5% dilutions from 5 different type extracts from grower A+B. 0.5 μL compound were place in each vial, 3 colony spots were added, the mixture was agitated in centrifuge with 6-8.000 rpm for 1.5 min and suspended in 500 μL PBS.

c. Staining Mounting: Staining kit Bacstain—CTC Rapid Staining kit BS02 was used. All 5 samples and 1 referral were stained. The Bacstain staining was applied for microbial cell viability assay. CTC (5-cyano-2,3-dytolyl tetrazolium chloride) was used to evaluate the microbial respiratory activity. Enhancing reagent was B. The 500 μL microbial suspension was treated with 10 μL CTC, and 2.5 μL reagent B. the suspension Incubated for 30 min at 37° C.

Figure 7A:
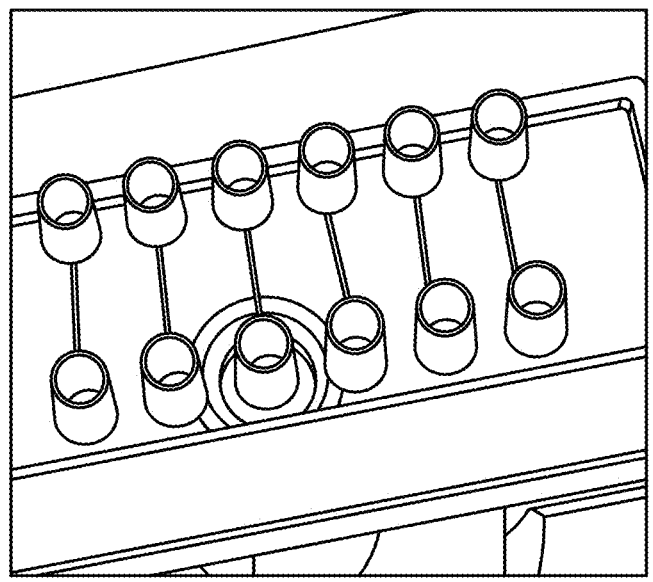
FIG. 7A is a photograph of an ibidi microslide dish with 6 channels.
Figure 7B:
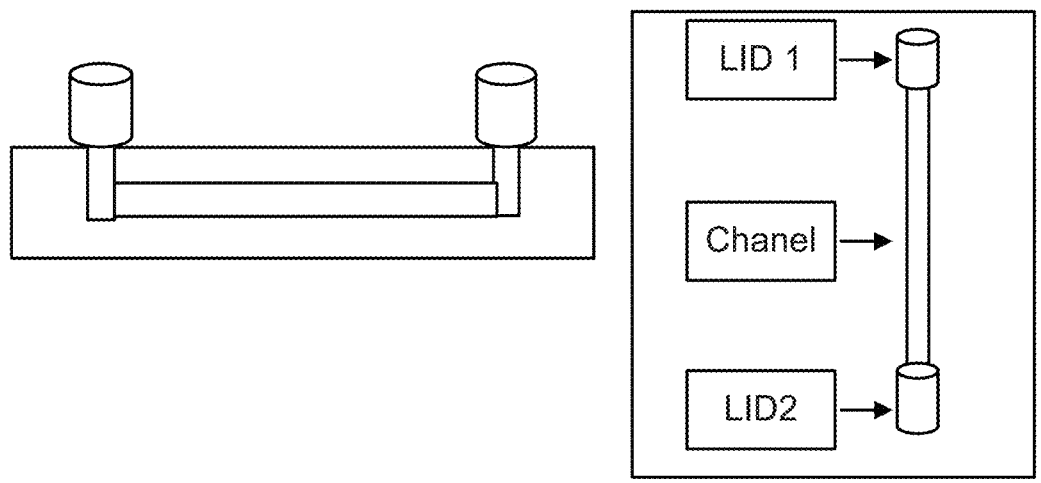
FIG. 7B is an illustration of a single channel of the ibidi microslide dish of FIG. 7A.

Mounting: A 4× Ibidi microslide dish with 6 channels 0.1 high was used (see FIG. 7A). 30 μL from the cells treated with 25% dilution of the cannabinoid of grower A were placed in $1^{st}$ LID channel and aspirated on the $2^{nd}$ LID (see FIG. 7B). Each channel was applied with different compound treated microbial cells, last one was the referral.

Figure 8:
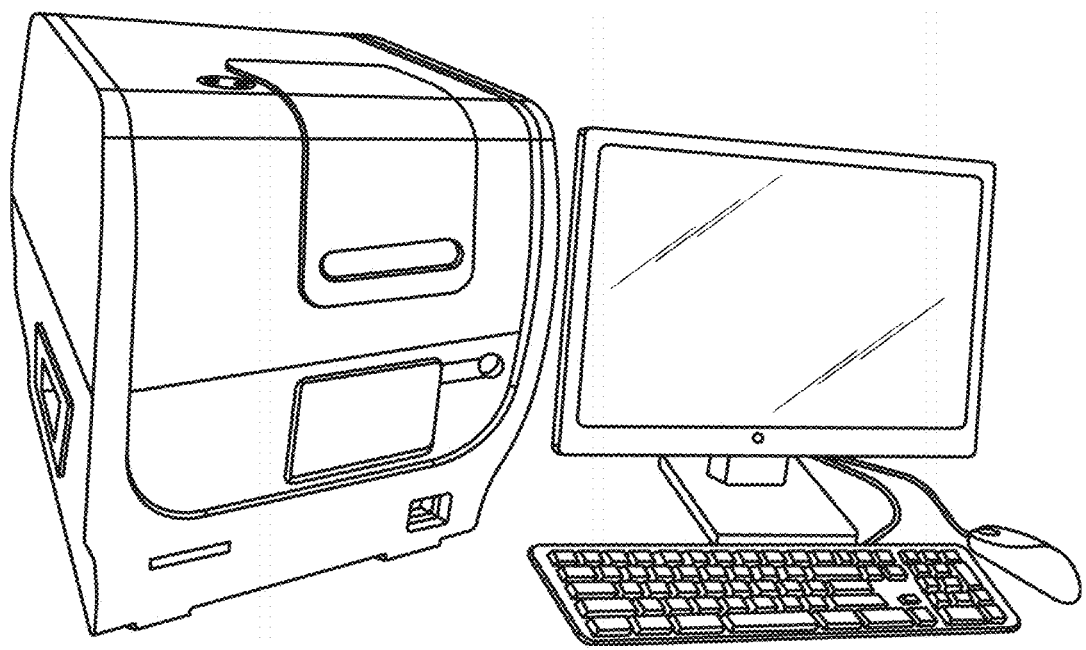
FIG. 8 is a photograph of a citation 5BioTex automated digital inverted microscope.

The same procedure was employed on the second slide with the cells treated with 25% dilution of the cannabinoid of grower B. Accordingly slide 3 had the cells from grower A with 12.5% dilution and slide 4 had the cells 12.5% dilution from grower B.

d. Imaging Imaging was preformed using a Cytation 5 BioTek (see FIG. 8). Cytation is a fully automated digital inverted microscope. Imaging modes include fluorescence, brightfield, color brightfield and phase contrast for a broad range of applications including live cell imaging, phenotypic assays, and 3D spheroids. Easily automate the acquisition, processing and analysis of images from microplates, slides, tissue culture dishes and flasks.

Figure 9:
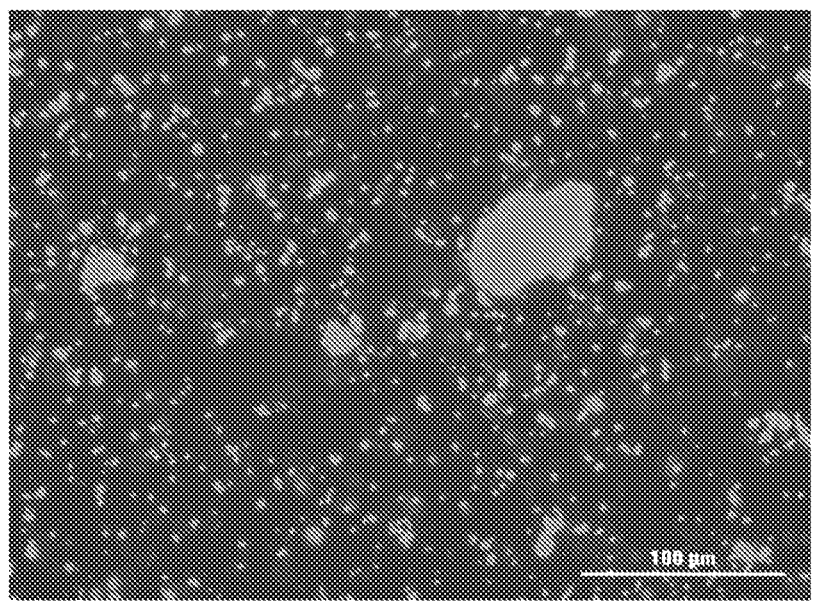
FIG. 9 is a set of microscope images of the dental plaque microbes taken at ×40 magnification.
Figure 9:
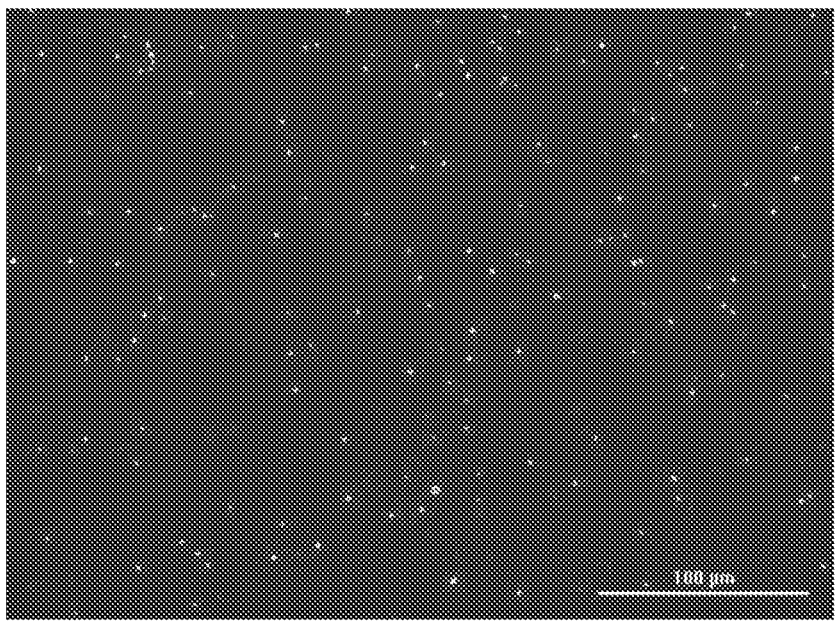
Figure 10:
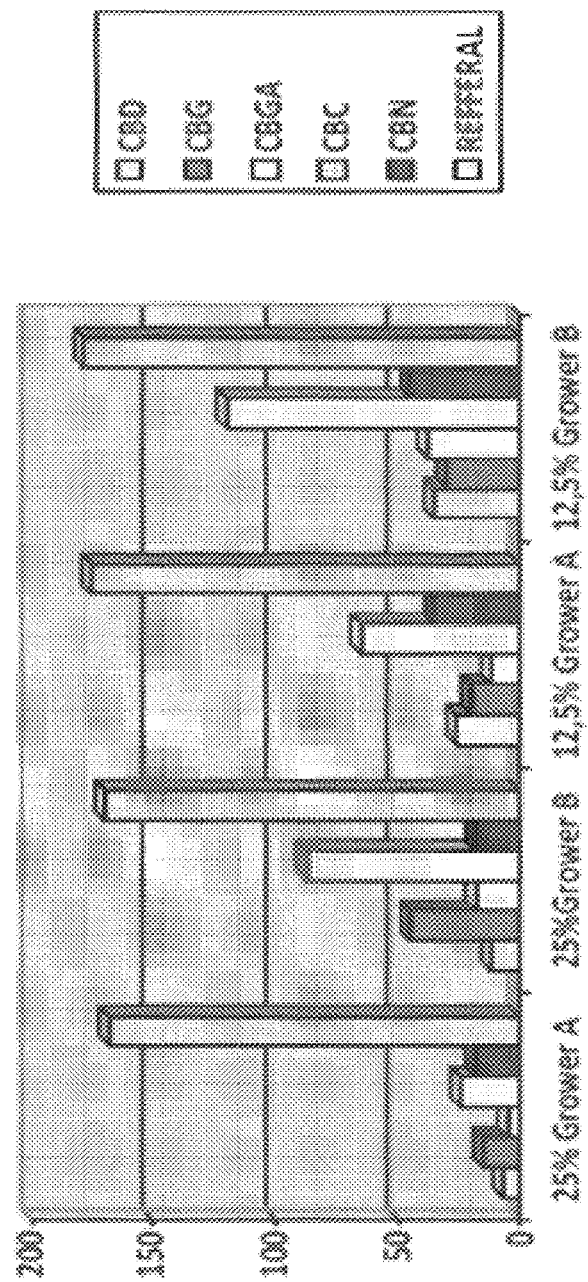
FIG. 10 is a graph depicting the effectiveness of the various cannabis compounds on number of dental plaque microbes while comparing the various cannabis compounds of two cannabis growers (Grower A vs. Grower B).

Cytation brings simplicity to the world of automated microscopy. With one click, fully the entire process is automated on hundreds of samples. In addition, Cytation integrates in one instrument the elaborate setup required for live cell imaging assays: automated stage, autofocus, temperature control, gas control, time-lapse imaging. Z-stacking, stitching and more. Forty (40) magnification was used for optimized detection of channel live cells, as well as using Z-Stacking and counting analyze. The two slides depict the bacteria of patient 1 taken from patient 1, following a referral (see FIG. 9A) treatment (n=5269 live cells) or CBG 25% dilution (see FIG. 9B) treatment (n=168 live cells).

e. Analyzing: FIG. 10 depicts the different efficacy of cannabinoids of grower A compared to cannabinoids of grower B, as well as the effect of the cannabinoid concentration (dilution) on live cells, derived from the consumers' dental plagues. The most efficient compounds on the plaque of the consumer, were CBGA 25% dilution of grower A. All compounds reduced the live cell counting in 70-85%. Here we can see specially CBGA-grower A was the best efficient (see FIG. 10).

f. The next step is to receive a consumer or patient's an inform consent regarding the recommended oral care; and g. Providing the consumer or patient's the basic cannabis or other antimicrobial oral health care.

The invention claimed is:

1. A system for providing a personalized oral care formulation for a patient, said system comprising:
   a. a detection module for detecting in vitro at least one of oral bacterial, viral and/or fungal infection in a sample of oral cavity obtained from said patient;
   b. an in vitro test module for testing antibacterial, antiviral and/or antifungal activity of a diagnostic panel of substances consisting of cannabinoids or cannabis related substances on said sample, the detection module and the in vitro test module being separated or combined in the same module; and
   c. an oral care compounding module for receiving data from said in vitro test module concerning effectiveness of compounds comprised in said panel on at least one of antibacterial, antiviral and/or antifungal activity in said patient's sample;

wherein said oral care compounding module provides instructions on producing a personalized oral care formulation comprising at least one member of said panel having a more effective antibacterial, antiviral and/or antifungal activity in vitro compared to other members of said panel.

2. The system of claim 1 further comprising an oral care compound cartridge containing said oral care formulation, optionally wherein the oral care compound cartridge is configured to be operationally connected to the patient's toothpaste package, dentifrice package or mouthwash container.

3. The system according to claim 1, wherein said oral care formulation is in the form of a mouthwash, dentifrice or toothpaste.

4. The system according to claim 1, wherein said oral care formulation further comprises at least one of chlorhexidine compounds, chlorhexidine gluconate, cationic antimicrobial compounds, essential oils, fluoride compounds, chlamoxicillin, amoxicillin/clavulanate, clindamycin, metronidazole, at least one herbal extract, optionally punica granatum extract, pomegranate extract, or any combination thereof.

5. The system according to claim 1, wherein said oral care compounding module is operationally connected to an oral care formulation production line.

6. The system according to claim 1, wherein said system additionally comprises a database for storing output of the patient results from the detection module, the in vitro test module or the oral care compounding module, or any combination thereof.

7. The system according to claim 1, wherein said system additionally comprises a server configured for processing and storing the patient's medical and/or dental data.

8. The system according to claim 4, wherein said cannabinoid is at least one of cannabinoid acid derivatives, optionally Tetrahydrocannabinolic acid (THCA), cannabidiolic acid (CBDA), cannabinolic acid (CBNA), cannabigerolic acid (CBGA), cannabichromenic acid (CBCA), cannabinodiolic acid (CBNDA), or any combination thereof.

9. The system according to claim 4, wherein said cannabinoid is an extract of any part of a cannabis plant and/or or a cannabinoid selected from the group consisting of Dronabinol, Nabiximols, Nabilone, Tetrahydrocannabinol (THC), Cannabidiol (CBD), Levonantradol, Ajulemic acid, Δ9-tetrahydrocannabinol, naturally occurring Δ9-THC, Cannabichromene (CBC), Cannabichromevarin (CBCV), Cannabichromevarinic acid (CBCVA), Cannabidiol monomethylether (CBDM), Cannabidiorcol (CBD-C1), Cannabidivarin (CBDV), Cannabidivarinic acid (CBDVA), Cannabielsoin (CBE), Cannabielsoic acid B (CBEA-B), Cannabielsoin acid A (CBEA-A), Cannabigerol (CBG), Cannabigerol monomethylether (CBGM),-Cannabigerolic acid monomethylether (CBGAM), Cannabigerovarin (CBGV), Cannabigerovarinic acid (CBGVA), Cannabinol (CBN)-, Cannabinodiol (CBND), Cannabinodivarin (CBVD), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), 10-Ethoxy-9-hydroxy-delta-6a-tetrahydrocannabinol, 8,9-Dihydroxy-delta-6a-tetrahydrocannabinol, Cannabitriolvarin (CBTV), Delta-8-tetrahydrocannabinol (Δ8-THC), Delta-8-tetrahydrocannabinolic acid (Δ8-

THCA), Delta-9-tetrahydrocannabinol (Δ9-THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Try-hydroxy-delta-9-tetrahydrocannabinol (triOH-THC), 3,4,5,6-Tetrahydro-7-hydroxy-alpha-alpha-2-trimethyl-9-n-propyl-2,6-methano-2H-1-benzoxocin-5-methanol, 8-OH-iso-HHCV, 9α-OH—HHC, and any combination thereof.

10. A method for providing a patient a personalized oral care formulation, the method comprising steps of:
   a. obtaining a sample from an oral cavity of said patient;
   b. incubating said sample in vitro for detecting at least one of oral bacterial, viral or fungal infection;
   c. in vitro testing antibacterial, antiviral and/or antifungal activity of a diagnostic panel of substances consisting of cannabinoids or cannabis related substances on said sample, the incubating and the testing, steps, (b) and (c), being separate steps or combined in the same step; and
   d. receiving data from said in vitro test concerning effectiveness of at least one compound comprised in said panel on at least one of antibacterial, antiviral, or antifungal activity in said patient's sample;
   e. providing instructions on producing a personalized oral care formulation comprising at least one member of said panel having a more effective antibacterial, antiviral and/or antifungal activity in vitro compared to other members of said panel; and
   f. administering the oral care formulation to said patient.

11. The method according to claim 10, wherein said oral care formulation is in the form of a mouthwash, dentifrice or toothpaste.

12. The method according to claim 10, wherein said oral care formulation further comprises at least one of chlorhexidine compounds, chlorhexidine gluconate, cationic antimicrobial compounds, essential oils, fluoride compounds, chlamoxicillin, amoxicillin/clavulanate, clindamycin, metronidazole-, at least one herbal extract, optionally punica granatum extract, pomegranate extract, or any combination thereof.

13. The method according to claim 10, wherein said method further comprises collecting and storing data of the patient, the data being medical and/or dental data.

14. The method according to claim 10, wherein said diagnostic panel of substances comprises cannabinoid acid derivatives, optionally at least one of THCA, CBDA, CBNA, CBGA, CBCA or CBNDA.

15. The method according to claim 10, wherein said diagnostic panel of substances comprises an extract of any part of a cannabis plant and/or or a cannabinoid which is at least one of Dronabinol, Nabiximols, Nabilone, THC, CBD, Levonantradol, Ajulemic acid, 49-tetrahydrocannabinol, naturally occurring Δ9-THC, CBC, CBCV, CBCVA, CBDM, CBD-C1, CBDV, CBDVA, CBE, CBL, CBEA-B, CBEA-A, CBG, CBGM, CBGAM, CBGV, CBGVA, CBN, CBND, CBDL, CBVD, CBNM, CBN-C2, CBN-C4, CBNA, CBN-C1, CBV, CBT, 10-Ethoxy-9-hydroxy-delta-6a-tetrahydrocannabinol, 8,9-Dihydroxy-delta-6a-tetrahydrocannabinol, CBTV, Δ8-THC, Δ8-THCA, Delta-9-tetrahydrocannabinol (Δ9-THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), OTHC, CBCF, CBF, Cannabiglendol, CBR, CBT, DCBF, Delta-9-cis-tetrahydrocannabinol (cis-THC), triOH-THC, 3,4,5,6-Tetrahydro-7-hydroxy-alpha-alpha-2-trimethyl-9-n-propyl-2,6-methano-2H-1-benzoxocin-5-methanol, 8-OH-iso-HHC, or 9α-OH—HHC.

16. A personalized oral care formulation for a patient provided by the method of claim 10, comprising at least one member of a diagnostic panel of substances consisting of cannabinoids or cannabis related substances previously tested in vitro in an oral sample from said patient and determined as being effective or having a greater antimicrobial, antiviral and/or antifungal activity compared to other antimicrobial, antiviral or antifungal compounds tested in vitro in the same oral sample of the same patient.

17. The personalized oral care formulation according to claim 16, wherein said oral care formulation further comprises at least one of chlorhexidine compounds, chlorhexidine gluconate, cationic antimicrobial compounds, essential oils, fluoride compounds, chlamoxicillin, amoxicillin/clavulanate, clindamycin, metronidazole, at least one herbal extract, optionally punica granatum extract, pomegranate extract, or any combination thereof.

18. The personalized oral care formulation according to claim 17, wherein said cannabinoid is at least one of cannabinoid acid derivatives, optionally THCA, CBDA, CBNA, CBGA, CBCA, CBNDA, or any combination thereof.

19. The personalized oral care formulation according to claim 17, wherein said cannabinoid is an extract of any part of a cannabis plant and/or or a cannabinoid selected from the group consisting of Dronabinol, Nabiximols, Nabilone, THC, CBD, Levonantradol, Ajulemic acid, Δ9-tetrahydrocannabinol, naturally occurring Δ9-THC, CBC, CBCV, CBCVA, CBDM, CBD-C1, CBDV, CBDVA, CBE, CBL, CBEA-B, CBEA-A, CBG, CBGM, CBGAM, CBGV, CBGVA, CBN, CBND, CBDL, CBVD, CBNM, CBN-C2, CBN-C4, CBNA, CBN-C1, CBV, CBT, 10-Ethoxy-9-hydroxy-delta-6a-tetrahydrocannabinol, 8,9-Dihydroxy-delta-6a-tetrahydrocannabinol, CBTV, Δ8-THC, Δ8-THCA, Delta-9-tetrahydrocannabinol (Δ9-THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), OTHC, CBCF, CBF, Cannabiglendol, CBR, CBT, DCBF, Delta-9-cis-tetrahydrocannabinol (cis-THC), triOH-THC, 3,4,5,6-Tetrahydro-7-hydroxy-alpha-alpha-2-trimethyl-9-n-propyl-2,6-methano-2H-1-benzoxocin-5-methanol, 8-OH-iso-HHCV, 9α-OH—HHC, and any combination thereof.

20. The personalized oral care formulation according to claim 16, wherein said oral care formulation is in a form of a mouthwash, dentifrice or toothpaste.

21. The method according to claim 10, wherein said diagnostic panel of substances comprises at least one of CBC, CBD, CBG, CBGA or CBN.

* * * * *